(12) United States Patent
Panin et al.

(10) Patent No.: US 12,141,898 B2
(45) Date of Patent: Nov. 12, 2024

(54) CONTINUOUS BED MOTION ACQUISITION WITH AXIALLY SHORT PHANTOM FOR PET IMAGING SYSTEM SETUP AND QUALITY CONTROL

(71) Applicant: Siemens Medical Solutions USA, Inc., Malvern, PA (US)

(72) Inventors: Vladimir Panin, Knoxville, TN (US); Mehmet Aykac, Knoxville, TN (US); Shikui Yan, Knoxville, TN (US); Brian Kelly, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 18/585,354

(22) Filed: Feb. 23, 2024

(65) Prior Publication Data

US 2024/0273783 A1  Aug. 15, 2024

Related U.S. Application Data

(62) Division of application No. 17/596,829, filed as application No. PCT/US2020/070589 on Sep. 29, 2020, now Pat. No. 11,961,164.

(Continued)

(51) Int. Cl.
*G06T 11/00* (2006.01)
*A61B 6/03* (2006.01)
*G16H 30/40* (2018.01)

(52) U.S. Cl.
CPC ............ *G06T 11/003* (2013.01); *A61B 6/037* (2013.01); *G06T 11/006* (2013.01); *G16H 30/40* (2018.01)

(58) Field of Classification Search
CPC ..... A61B 6/037; G06T 11/003; G06T 11/006; G16H 30/40
See application file for complete search history.

(56) References Cited

U.S. PATENT DOCUMENTS

2012/0070050 A1   3/2012   Panin et al.
2014/0200848 A1   7/2014   Panin et al.
(Continued)

FOREIGN PATENT DOCUMENTS

CN   108703769   10/2018
EP   3399346     11/2018
(Continued)

OTHER PUBLICATIONS

Panin, et al., "Self-Time Alignment Method for Patient-Based Quality Control", 2017 IEEE Nuclear Science Symposium and Medical Imaging Conference (NSS/MIC), IEEE, Oct. 21, 2017 (Oct. 21, 2017), pp. 1-5.
(Continued)

*Primary Examiner* — Mark R Gaworecki

(57) ABSTRACT

An improved method for time alignment (TA) procedure and crystal efficiency (CE) normalization estimation procedure for a PET scanner system is disclosed. In the TA procedure modeled time-of-flight (TOF) data are compared against the measured TOF data from an axially short cylinder phantom in order to find individual detector's time offsets (TOs). Then the TOs are estimated simultaneously by matching the TOF center of mass between the modeled and measured TOF data. In the CE estimation, TOF reconstruction of CBM data on the axially short cylinder phantom is performed. Alternating between TOF image reconstruction and CE updates eventually lead to the correct estimation of activity and CE component.

7 Claims, 15 Drawing Sheets

Related U.S. Application Data

(60) Provisional application No. 62/912,817, filed on Oct. 9, 2019.

(56) References Cited

U.S. PATENT DOCUMENTS

| | | |
|---|---|---|
| 2015/0036789 A1 | 2/2015 | Panin et al. |
| 2017/0082759 A1 | 3/2017 | Lyu et al. |
| 2017/0194735 A1 | 7/2017 | Arai |
| 2018/0322626 A1 | 11/2018 | Panin |
| 2020/0033491 A1 | 1/2020 | Panin |

FOREIGN PATENT DOCUMENTS

| | | |
|---|---|---|
| WO | 2010084528 | 7/2010 |
| WO | 2014066629 | 5/2014 |

OTHER PUBLICATIONS

International Search Report for Corresponding PCT Application No. PCT/US2020/070589, dated Apr. 15, 2021.

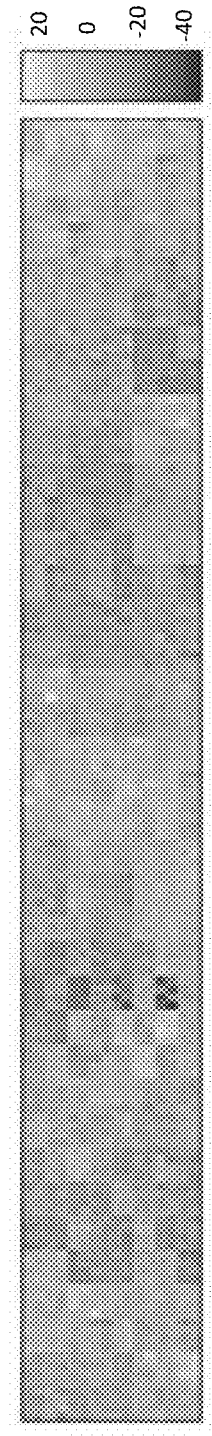
FIG. 9A (Standard TA)
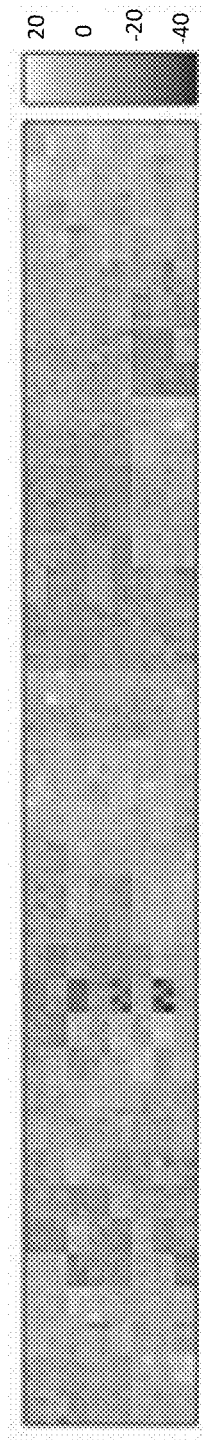
FIG. 9B (CBM TA)
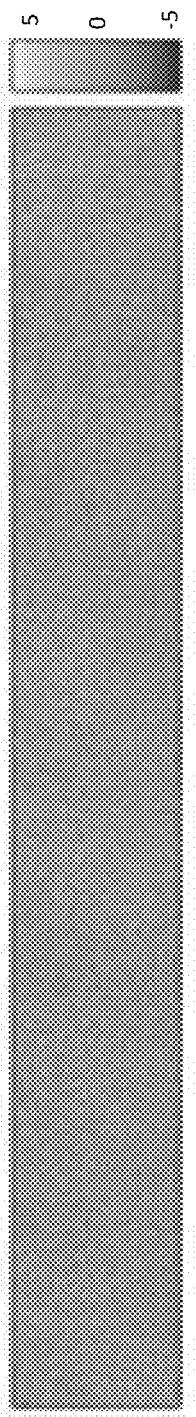
FIG. 9C (Difference)

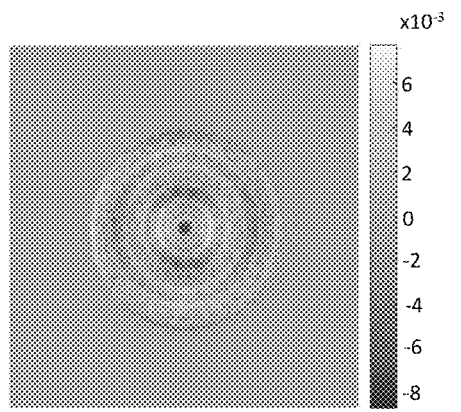
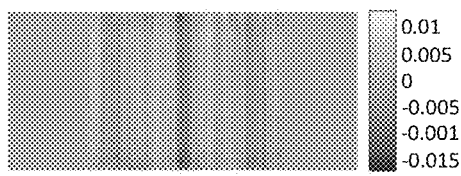
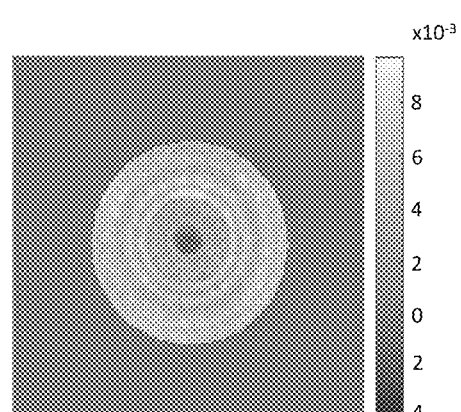
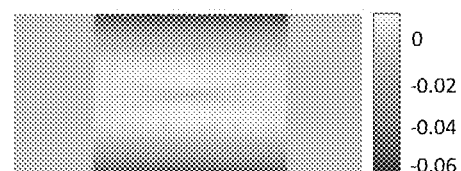
FIG. 11A  FIG. 11B

CONTINUOUS BED MOTION ACQUISITION WITH AXIALLY SHORT PHANTOM FOR PET IMAGING SYSTEM SETUP AND QUALITY CONTROL

CROSS-REFERENCE TO RELATED APPLICATIONS

This application is a divisional of U.S. patent application Ser. No. 17/596,829, filed Dec. 20, 2021, which is a 371 application of PCT Application No. PCT/US2020/070589, filed Sep. 29, 2020, which claims priority under 35 U.S.C. § 119(e) to U.S. Provisional Application No. 62/912,817 filed on Oct. 9, 2019, the entire contents of which are incorporated herein by reference.

FIELD

The present disclosure is generally related to medical imaging, and more specifically to system and method time alignment calibration and crystal efficiency normalization for continuous bed motion acquisition mode in positron emission tomography (PET) systems.

BACKGROUND

PET is a modality of nuclear medicine for imaging metabolic processes by employing gamma photons emanated from radiopharmaceuticals ingested by a patient or injected into a patient. Multiple PET data are taken in multiple directions to generate/reconstruct a 3-dimensional PET image and/or multiple slices of a PET image. Before image reconstruction, PET raw image data are in projection/sinogram space. PET scanning generally provides useful information regarding the functional condition of the body tissues and systems such as the cardiovascular system, respiratory system, and/or other systems. PET scanning is useful for indicating the presence of soft tissue tumors or decreased blood flow to certain organs or areas of the body.

Time alignment (TA) procedure refers to the process of calibrating a PET scanner for any residual time offsets between two detectors in coincidence. While the hardware and electronics are matched as carefully as possible, some timing differences can remain. These timing differences reduce the performance of a time-of-flight (TOF) PET scanner since the TOF PET scanner detects the position of a coincidence event along a line of response (LOR). To ensure correctness of time information in TOF data, TA procedure is performed on a regular basis for TOF PET scanners.

TOF data reconstructed images display less sensitivity to data inconsistencies, such as systematic errors in the correction factors. On the other hand, the quality of TOF reconstruction strongly depends on the correctness of time information. In order to ensure accurate time information for TOF reconstruction in PET scanners, a TA procedure, also referred to as timing calibration, is performed on a regular basis in PET scanners. An example of TA calibration for a PET scanner system is disclosed in U.S. Pat. No. 8,089,043, issued Jan. 3, 2012, the contents of which are incorporated herein by reference.

In general, a test object (phantom) is used to calibrate and/or verify (QC) the accuracy of nuclear medical imaging devices such as PET scanners. A phantom is an object that contains positron (β+) emitting activity in a known shape and distribution throughout its body. Thus, by imaging the phantom, the accuracy of the PET instrument and its software may be assessed and, if necessary, the settings may be adjusted.

Conventionally, PET, PET/CT, and PET/MR systems are quality controlled and calibrated using a cylindrical phantom, comprised of $^{68}$Ge, as the positron source, dispersed in a solid urethane matrix, and encased in a polyethylene shell. The cylindrical shape facilitates subsequent analysis through symmetry.

For TA procedures, a uniform activity cylindrical phantom is placed at the center of the detector's field of view (FOV). It is assumed that all LORs originating from a particular detector have TOF center of mass centered at zero. Then, each crystal time offset (TO) is chosen accordingly. Generated TOs are stored in the system and used during data rebinning in every LOR TOF information shift, which is a combination of coincidence crystal TOs.

The cylindrical phantom is longer than the axial extent of the imaging volume, so dimensions of 21 cm diameter×35 cm long are typical. The phantoms are quite heavy, about 10-15 kg, and require over 100 kg of lead for shielding the technologist, the scanner, patients and other people, from the bulk of the annihilation gamma photons when not in use.

In modern PET scanners, the PET scanner lengths are becoming longer in an attempt to lengthen the FOV and thus gain sensitivity. Scaling the phantoms to match the longer FOV of these PET scanners with ever increasing axial extent is impractical as there is excessive attenuation and scatter of the gamma photons, and the phantoms become excessively heavy and difficult to shield when in storage.

The development of silicon photomultiplier (SiPM) based detectors resulted in significant improvement of TOF resolution in PET scanning. For example, a Siemens new generation SiPM prototype PET/CT scanner has reached TOF resolution of about 250 ps. However, because of the improved TOF resolution in SiPM based detectors, higher standard in validating TOF information is required since TOF reconstruction is sensitive to any misplacement of events based on inaccurate time measurement.

Generally, PET scanner quality control (QC) procedure is performed on a daily basis on a uniform cylinder phantom for PET scanner calibration that involve crystal efficiency (CE) estimation and time alignment (TA). However, such phantoms have been relatively bulky and heavy and not necessarily optimal in the clinical environment. Recently, self-correction methodologies such as patient-based QC procedures for TA and CE estimation for arbitrary objects, including patients, have been introduced.

Therefore, a need exists for an improved TA and CE estimation procedures that provides more accurate system set up for QC procedure for long FOV PET scanner systems.

SUMMARY

Disclosed herein are novel methods of improving TA and CE estimation procedures for PET scanner systems with long FOV by using an axially short calibration phantom that has a shortened overall length than conventionally used calibration phantoms.

Continuous bed motion (CBM) acquisition and reconstruction is currently the standard on many PET scanners. This type of acquisition opens the possibility of using axially short and consequently light phantoms for system setup. In CBM acquisitions, counts from various detector pairs are combined together, taking the bed motion into account. While this is beneficial for exact activity reconstruction, axial detector structure is lost due to the averaging over motion. For a feasible estimation of detector properties, additional "stationary" data similar to the step and shoot (S&S) data are produced. In this complementary set, activity is integrated over motion while preserving the detector axial structure. The same rebinner can be used to generate both data sets; in one case motion is integrated into the rebinning process and in the second case it is ignored. Using the two complementary data sets, the simultaneous reconstruction of PET activity and PET detector properties is achievable in CBM.

Disclosed herein is a TA set up procedure and crystal efficiency (CE) normalization estimation using an axially short uniform phantom during a CBM system setup. While a CBM "stationary" scan is naturally uniform in the axial direction, the exact modeling of these data requires reconstruction of CBM data. The present disclosure relates to the improvement of the TA setup and CE estimation.

In the TA set up procedure, CBM data are produced without TOF information, since TOs are not known at that moment. These data are reconstructed by ordinary non-TOF CBM reconstruction methodology.

The complementary data set, acquired in a stationary system of coordinates, is modeled as motion-blurred TOF projection of images from previous step reconstructions. Note that attenuation is included in the blurring operation, as it is not separate from the activity projection. Produced modeled TOF data are used in the TA procedure based on data momentums.

In some embodiments, a method for time alignment (TA) for a PET scanner system is disclosed. The method comprises receiving list mode data; generating non-time of flight (TOF) projection data, scanner efficiency normalization array n, and attenuation factor a; reconstructing image f from the non-TOF projection data, corrected for scanner efficiency by a normalization array n, and for attenuation by attenuation factor a; modeling non-TOF and TOF scatter S and non-TOF and TOF projections $\bar{p}$; for each line of response, modeling TOF center-of-mass (modeled TOF COM) of true coincidence distribution from zero and first order moments $M_0$ and $M_1$ of the modeled TOF data; for each line of response, computing measured TOF center-of-mass (measured TOF COM); and determining TOF time offsets, to, by taking the difference between the measured TOF COM and the modeled TOF COM.

In the CE estimation procedure, TOF reconstruction of CBM data taken of an axially short phantom is performed. Alternating between TOF image reconstruction and CE updates eventually lead to the correct estimation of activity and the CE component, up to a scaling parameter. The CE estimation from rotating rod acquisition (used to derive all normalization components) is used in the only image TOF reconstruction followed by the CE update by ten iterations of the maximum likelihood alternating conditional expectation (ML-ACE) algorithm described in V. Y, Panin, "Simultaneous activity and crystal efficiencies reconstruction: TOF patient-based detector quality control," IEEE MIC 2014.

By using an axially short cylindrical phantom in TA and CE estimation procedures, axially longer FOV of the axially longer PET scanners by moving the short cylinder through the longer FOV.

In some embodiments, a non-transitory, machine-readable storage medium encoded with program instructions for controlling a PET scanner is disclosed. When a processor executes the program instructions, the processor performs the method for TA and/or the method for CE estimation for a PET scanner as disclosed herein.

BRIEF DESCRIPTION OF THE DRAWINGS

FIGS. 9A-9C show detector crystal TO estimations by two different methods and their differences.

FIG. 11A shows the normalized difference image of a uniform cylinder using CBM axially short cylinder phantom derived reconstruction and standard normalization derived reconstruction. The view on the top portion is the transaxial view and the view on the bottom portion is the coronal view.

FIG. 11B shows the normalized difference image of the uniform cylinder using virtual cylinder derived reconstruction and standard normalization derived reconstruction. The view on the top portion is the transaxial view and the view on the bottom portion is the coronal view.

DETAILED DESCRIPTION

This description of the exemplary embodiments is intended to be read in connection with the accompanying drawings, which are to be considered part of the entire written description.

Figure 1:
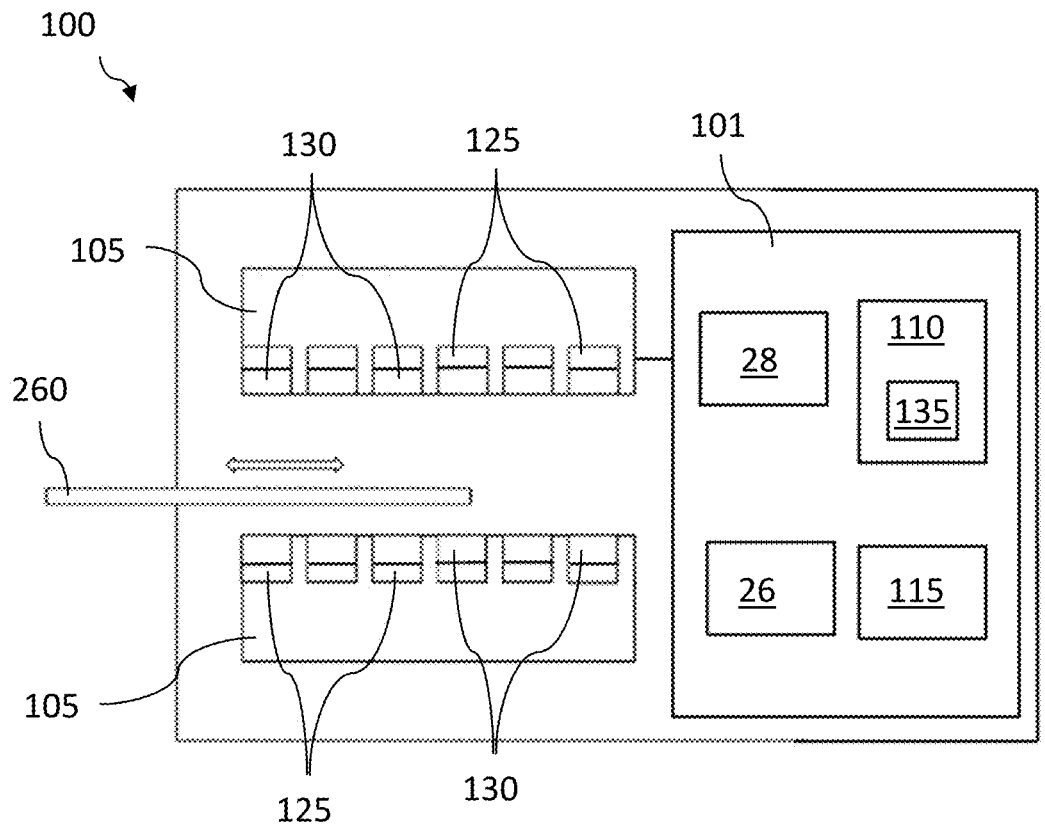
FIG. 1 is a high-level block diagram of a PET scanner system having a time alignment calibration manager in accordance with an embodiment of the present disclosure.

FIG. 1 is a high-level schematic diagram of a PET scanner system 100 comprising a PET detector ring 105, a control unit 101, and a patient bed 260. The control unit 101 can comprise a central controller 28, any necessary memory 26, a coincidence processor 110, a TA manager 135, and an image reconstruction unit 115. The TA manager 135 is a microprocessor suitably configured for executing the TA procedures disclosed herein. The PET detector ring 105 comprises scintillator crystals 130 and photomultipiers 125 that are provided in ring configuration surrounding the patient tunnel in which the patient bed 260 travels into and out of.

In general, a living subject, e.g. a patient, is injected with a short-lived radioactive tracer isotope (e.g., usually into blood circulation) before conducting a PET scan. The tracer isotope is for example fluorodeoxyglucose (FDG), which is a type of sugar. During the PET scan, data is recorded from the tracer-concentrated tissue as the tracer isotope decays.

As the tracer-concentrated tissue undergoes positron emission decay, the tissue emits a positron, which is an antiparticle of the electron with opposite charge. The positron eventually collides with an electron, producing a pair of annihilation (gamma) photons moving in opposite directions. The gamma photons are detected when they reach the scintillator crystals 130 in the PET detector ring 105, creating a burst of light which is detected by the photomultipliers 125. The pair of photons move in approximately opposite direction and are processed to determine whether the detected pair of photons originated from a coincidence event by the coincidence processing unit 110. If so, signals representing the detected pair of photons are sent to the image reconstruction unit 115 for an image data that is generated using mathematical image reconstruction procedures.

TA Set Up Procedure

The coincidence processing unit 110 includes the TA manager 135, which facilitates calibrating the PET detectors for any residual TOs between two detectors in coincidence. Although the TA manager 135 is shown to be a part of the coincidence processing unit 110, the TA manager 135 can be a separate independent unit or part of another component of the PET system 100, such as the image reconstruction unit 115.

Figure 2:
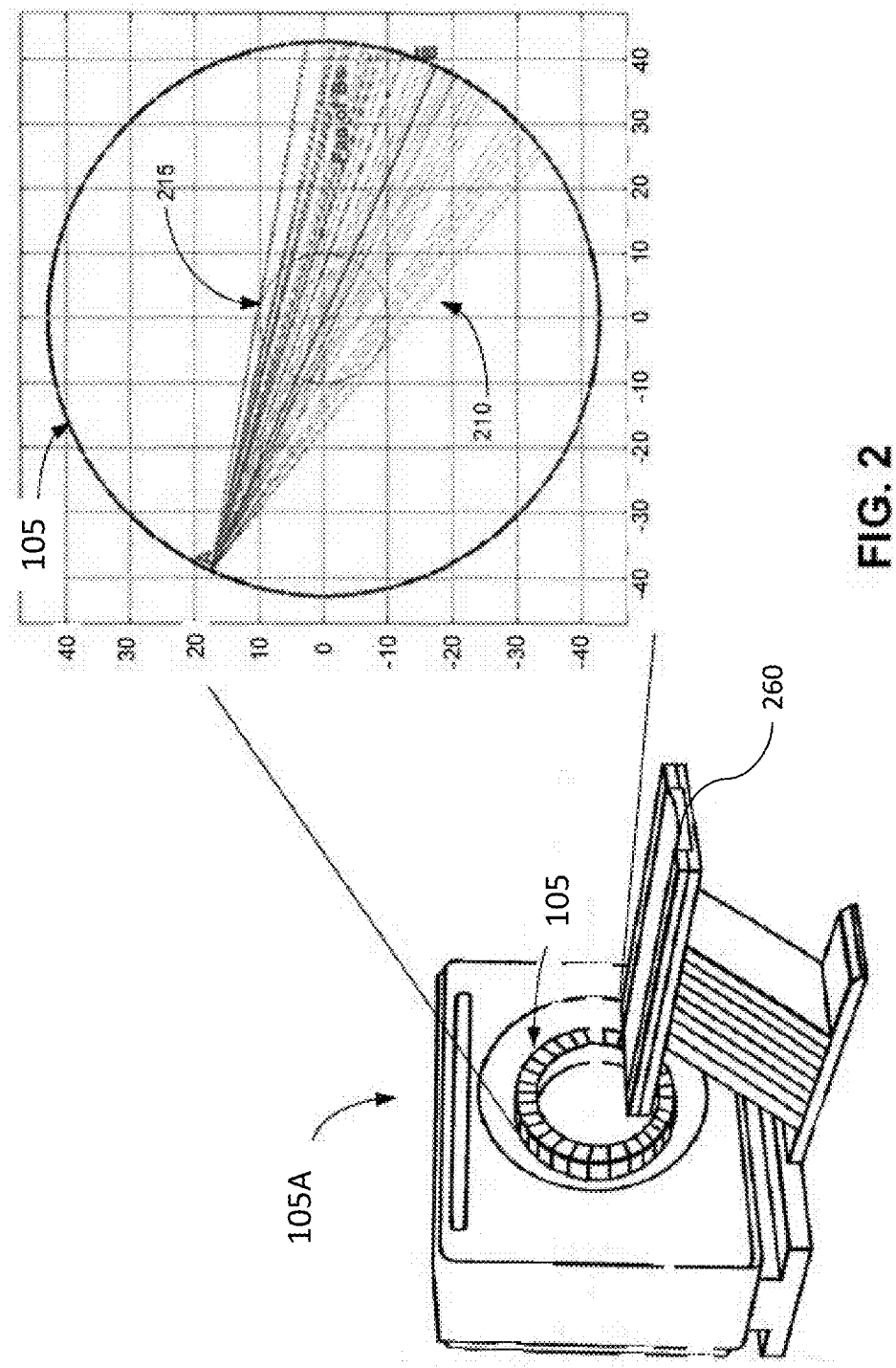
FIG. 2 is a perspective view of a PET scanner detector and a two-dimensional front view of a ring detector that is used with a phantom in accordance with an embodiment of the present disclosure.

FIG. 2 is a perspective view of a PET detector having a detector ring 105 in accordance with an embodiment of the present disclosure. In this example, the detector ring 105 is a part of a PET gantry 105A and has a radius 427.6 mm with 672 crystals/gaps (e.g., crystals A and B). The CBM patient bed 260 is positioned in front of the PET gantry 105A. On the right side of FIG. 2 is a schematic expanded illustration of the detector ring 105 showing example LORs 210 through the FOV 215 between detector crystal A to detector crystal B.

The TOF event is a time difference of a coincidence event that reaches crystal A minus the time the coincidence event that reaches crystal B. One skilled in the art would appreciate that a position of the TOF event can be calculated from the time difference of the coincidence. The position of the TOF event can be determined somewhere on the LOR. In calculating TOs, positive time direction is generally from detector crystal A to detector crystal B.

A TA procedure for calibrating the time alignment for the PET detector 105 using an axially short phantom is described herein. In the TA procedure described herein, the list mode data file for the axially short phantom is available and a CT scan of the axially short phantom does not need to be taken because the parameters of the axially short phantom is known and can determine the position of the phantom from PET data. In some embodiments, however, a CT scan can be taken of the axially short phantom.

The TA procedure in CBM acquisition mode described herein is the similar to the generalized self-TA procedure disclosed in U.S. patent Application publication No. 2020/0033491A1 for using patient CBM scan data. The disclosure of U.S. patent Application publication No. 2020/0033491A1 is incorporated by reference herein. However, here, CBM scan data of an axially short phantom is utilized for accurate TA estimate.

TO (Crystal Time Offset) Estimation

TOF prompt data set y with spatial (radial ($\rho$), azimuthal ($\theta$), and axial ($\zeta$), which includes polar angle segments) projection index ($\rho,\theta,\zeta$) and TOF bin index T can be modeled by combining the modeled projection from the emission object f, defined by voxel index k, corrected for scanner efficiency by a normalization array n and for attenuation by a, and scatter estimation S, corrected for scanner efficiency as well, and mean random data $\bar{r}$ by using the following equation (1):

$$\bar{y}_{\rho\theta\zeta T} = a_{\rho\theta\zeta} n_{\rho\theta\zeta}^{-1} \sum_k C_{\rho\theta\zeta T,k} f_k + n_{\rho\theta\zeta}^{-1} S_{\rho\theta\zeta T} + \bar{r}_{\rho\theta\zeta T} \quad (1)$$

where $\bar{y}_{\rho\theta\zeta T}$ is the mean of the TOF prompt data set y, C is the geometrical projection system matrix. In non-TOF notations, the T index will be omitted, since summation over T is performed. According to the recognized normal convention, the variables with a bar "-" above the variable denotes mean values.

Figure 3A:
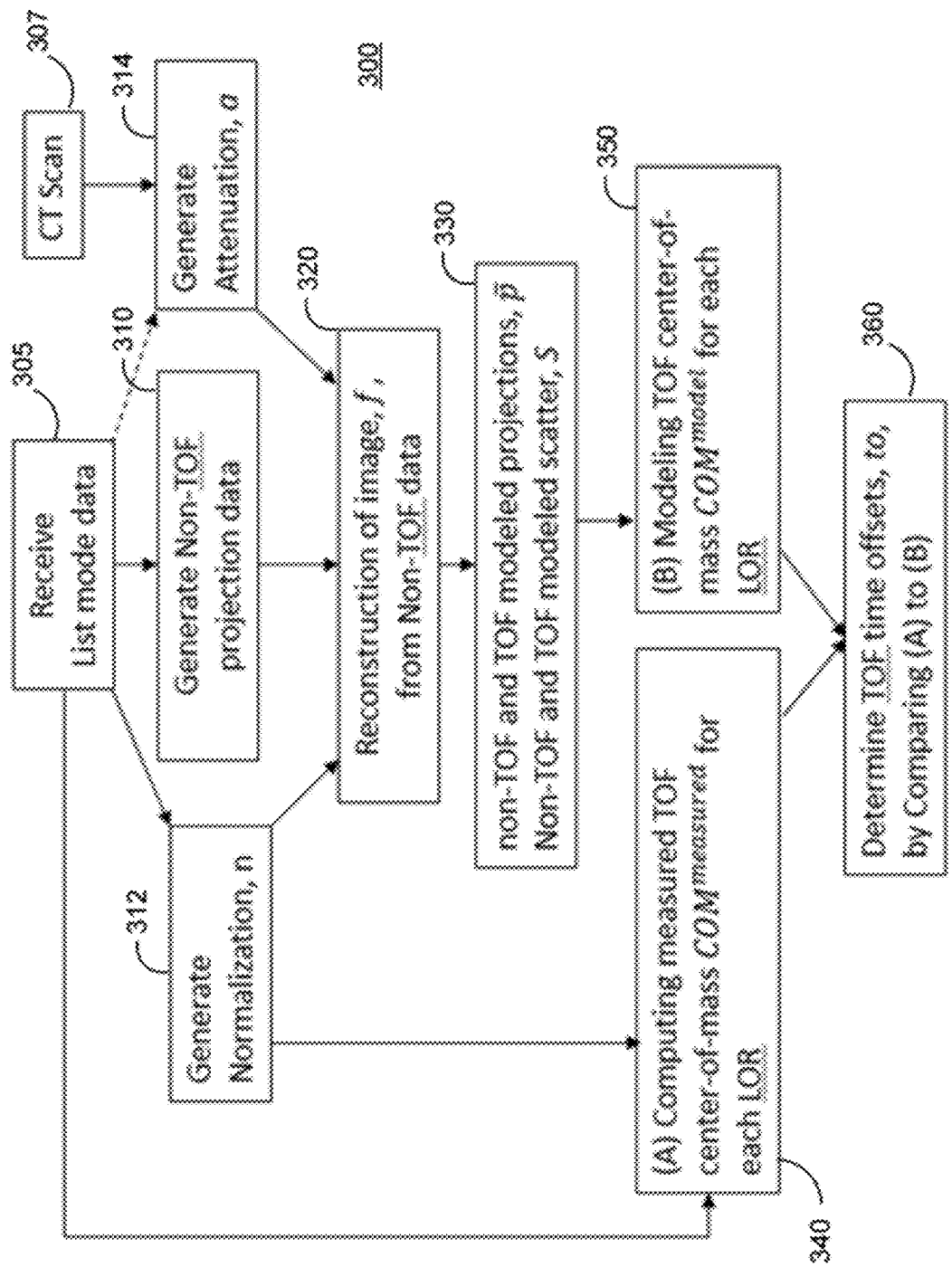
FIG. 3A is a flowchart 300 illustrating the TA procedure of the present disclosure.

FIG. 3A is a flowchart 300 illustrating the TA procedure of the present disclosure performed by the TA manager 135. Referring to the flowchart 300, in some embodiments, the system's TA manager receives list mode data from PET scan of an axially short cylinder phantom (box 305). The emission data used does not require a CT scan of the phantom. From the list mode data, non-TOF projection data is generated (box 310), along with normalization array n (box 312), and attenuation factor a (box 314). One of ordinary skill in the art of medical imaging technology would readily understand how to generate these from the list mode data.

The flowchart 300 also covers another option for attenuation correction, where the attenuation is obtained by a CT scan of the axially short cylinder phantom (box 307).

Next, image f is reconstructed from the non-TOF projection data (box 320), corrected for scanner efficiency by the normalization array n, and for attenuation by the attenuation factor a. Knowing f, in step 330, non-TOF and TOF scatter S and non-TOF and TOF projections $\bar{p}$ are modeled. It will be noted here that f, n, a, S, and $\bar{p}$ are vectors as they would be readily understood by those of ordinary skill in the art of medical imaging technology.

Then in step 350, for each LOR, modeled TOF center-of-mass (COM) data, $COM_{\rho\theta\zeta}^{model}$, of true coincidence distribution is estimated by modeling from zero order and first order moments $\bar{M}_0$, $\bar{M}_1$ of the modeled TOF data $\bar{p}_{\rho\theta\zeta T}$. This is carried out using the following equation group (2):

$$COM_{\rho\theta\zeta}^{model} = \frac{\bar{M}_1(\rho\theta\zeta)}{\bar{M}_0(\rho\theta\zeta)},$$

where $$\bar{M}_1(\rho\theta\zeta) = \sum_T T\bar{p}_{\rho\theta\zeta T}, \bar{M}_0(\rho\theta\zeta) = \sum_T \bar{p}_{\rho\theta\zeta T}, \text{ and}$$

$$\text{and } \bar{p}_{\rho\theta\zeta T} = a_{\rho\theta\zeta} \sum_k C_{\rho\theta\zeta T,k} f_k + S_{\rho\theta\zeta T}.$$

Note that normalization is not needed (canceled over the numerator and denominator) in the COM estimation per each LOR. Note that $M_0$ is independent of time resolution model. Meaning that $M_0$ will stay same for any resolution of scanner, e.g. 250 or 500 ps. Moreover, if in reality TOF profile was not Gaussian, but other symmetrical profile, $M_0$ will still be the same value. $M_1$ is also independent of time resolution model in true unscattered part, assuming normalized symmetrical TOF kernel. This can be an important advantage of this inventive method, since uniform (across various LORs) time resolution cannot be guaranteed and its exact knowledge may not be necessary.

In list mode processing, represented by step 340, measured TOF COM, $COM^{measured}$, is computed for each LOR as well using the following equation group (3):

$$COM^{measured}_{\rho\theta\zeta} = \frac{n_{\rho\theta\zeta} M_1(\rho\theta\zeta)}{\overline{M}_0(\rho\theta\zeta)},$$

where $COM_{\rho\theta\zeta}^{measured}$ is the measured TOF COM, and $$M_1(\rho\theta\zeta) = \sum_T T(y_{\rho\theta\zeta T} - r_{\rho\theta\zeta T}).$$

Note that the total mass $M_0$ in the denominator is computed by using modeled data instead of measured data to suppress noise magnification by division. LOR normalization (which is normalization coefficient computed for every LOR individually) is used on measured data. In previous notation, sinograms are compressed data, which is projection bin containing more than one LOR. Consequently, normalization is combined over LORs for sonogram data. Projection data of list mode are not compressed, each bin contain one LOR. Computation of $M_1$ involves subtraction of delayed event r and summation of prompt event y.

In step 360, the TOF time offsets, to, is determined. This is accomplished by taking the difference, $\Delta_{\rho\theta\zeta}$, between the measured TOF COM, $COM_{\rho\theta\zeta}^{measured}$, from equation group (3) and the modeled TOF COM, $COM_{\rho\theta\zeta}^{model}$, mean values from the equation group (2): $\Delta_{\rho\theta\zeta} = COM_{\rho\theta\zeta}^{measured} - COM_{\rho\theta\zeta}^{model}$.
$\Delta_{\rho\theta\zeta}$ is defined by individual detector crystals, denoted by indices i and j, and TO is denoted by to. An unweighted Gaussian model is used in the optimization procedure to estimate the TOs:

$$\min_{to} L = \frac{1}{2} \sum_{i \neq j} \omega_{\rho\theta\zeta, ij} (\Delta_{\rho\theta\zeta} - to_i + to_j)^2, \quad (4)$$

wherein L is the least squares difference between measured and modeled time shifts, and ω is the LOR contribution factor defined as:

$$\omega_{\rho\theta\zeta, ij} = \begin{cases} 1, & \text{if } ij \text{ contribute to sinogram bin}(\rho, \theta, \zeta) \\ 0, & \text{otherwise} \end{cases}.$$

Note that the contribution factor w keeps track of the ordered i,j pair, since the TOF information is directional. The following equation (5) is the Coordinate Descent (CD) optimization algorithm update equation:

$$to_i^{(m,l)} = \frac{1}{N_i}\left(\sum_j \omega_{\rho\theta\zeta, ij} \Delta_{\rho\theta\zeta} + \sum_j to_j^{(m,l-1)}\right),$$

where $$N_i = \sum_j \omega_{\rho\theta\zeta, ij}. \quad (5)$$

In equation (5), l is the sub-iteration number in sequential updates of individual crystal TO and m is the iteration number, when all crystals were updated once. Note that equation (5) contains the fan-sum of data, originated in the crystal i, and $N_i$ denotes the number of LORs in coincidence between crystal i and all possible crystals j.

Since TOs are defined only up to additive constant, after each iteration of the algorithm, TO is updated by a constant factor ∀ to ensure property:

$$\forall \, m \sum_i to_i^{(m)} = 0 \quad (6)$$

CBM Acquisition Case for TA Procedure

The scheme of the method for determining TOs is also applicable to CBM acquisition case.

Figure 4A:
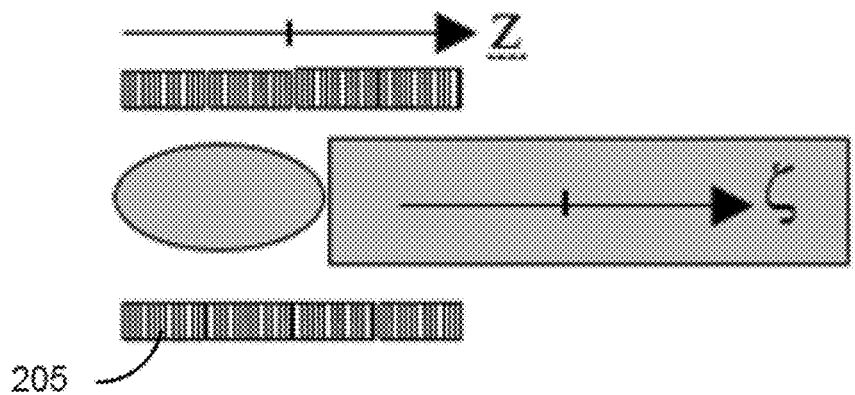
FIGS. 4A and 4B illustrate the two coordinate systems in CBM acquisition set up. Only axial axis is labeled.
Figure 4B:
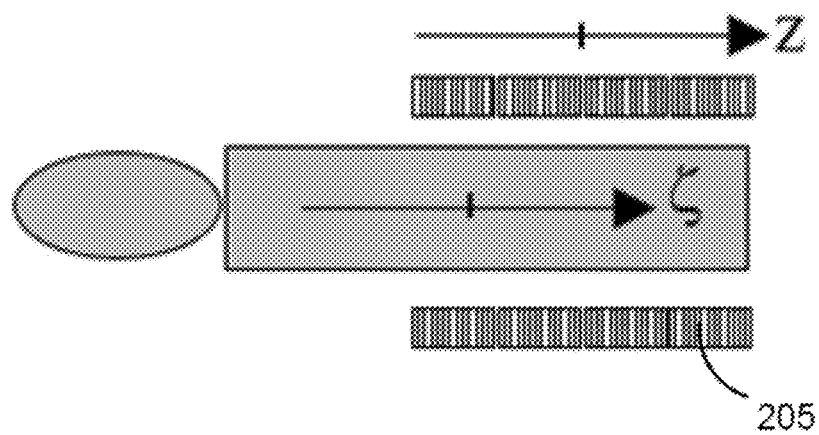

There are two coordinate systems to contend with in a CBM acquisition as shown in FIGS. 4A and 4B. One is the coordinate system of the room, which is aligned with the scanner. In the second, the room and the scanner are moving, and the patient is stationary. Scanner data are represented by axial plane coordinate z, which includes a polar angle. The moving object virtual LORs have the same transaxial coordinates, but are described by different axial coordinates ζ. We denote a function in which we map coordinate ζ onto the scanner system coordinate as Z (ζ, t), where t is acquisition time duration. This function uses object/bed axial motion knowledge. The function aligns the room and moving scanner system axial coordinates with the nearest neighbor approximation in order to preserve Poisson statistics during data rebinning. The rebinner produces two types of data: CBM for activity reconstruction, and stationary for TO estimation. Activity, the PET image, is reconstructed from CBM non-TOF projection data. The complementary data set COM, acquired in a stationary system of coordinates, is modeled using the following equation group (7):

$$COM_{\rho\theta z}^{model} = \frac{\overline{M}_1(\rho\theta z)}{\overline{M}_0(\rho\theta z)}, \quad (7)$$

$$\overline{M}_1(\rho\theta z) = \sum_T T \overline{p}_{\rho\theta z T},$$

$$\overline{M}_0(\rho\theta z) = \sum_T \overline{p}_{\rho\theta z T},$$

$$\overline{p}_{\rho\theta z T} = B\left(a_{\rho\theta\zeta} \sum_k C_{\rho\theta\zeta T, k} f_k + S_{\rho\theta\zeta T}\right)$$

where $COM_{\rho\theta\zeta}^{model}$, $\overline{M}_0$, and $\overline{M}_1$ are as defined above for stationary bed system.

The modeled TOF data $\overline{p}_{\rho\theta\zeta T}$ is modified by the blurring operator B to account for the blurring during the bed motion in CBM mode. The blurring operator B due to the CBM motion can be denoted as $$B(\bar{p}_{\rho\theta\zeta T}) = \int_0^{t'_{acq}} dt' \sum_{\zeta} e^{-\lambda t} d_{\rho\theta z}(t) \bar{p}_{\rho\theta\zeta T} \delta_{z,Z(\zeta,t)} \quad (8)$$

where λ is the decay correction constant for a specific isotope, δ is Kronecker's delta, d is the dead time correction factor, and t is acquisition time. Note that the definition of the modeled data $\bar{p}$ includes attenuation in the blurring operation.

Once motion blurred modeled COM data are defined, measured COM is computed according to the expressions (3), now in scanner system of coordinates, and the TO estimation procedure is the same as that described in (4)-(6).

Figure 3B:
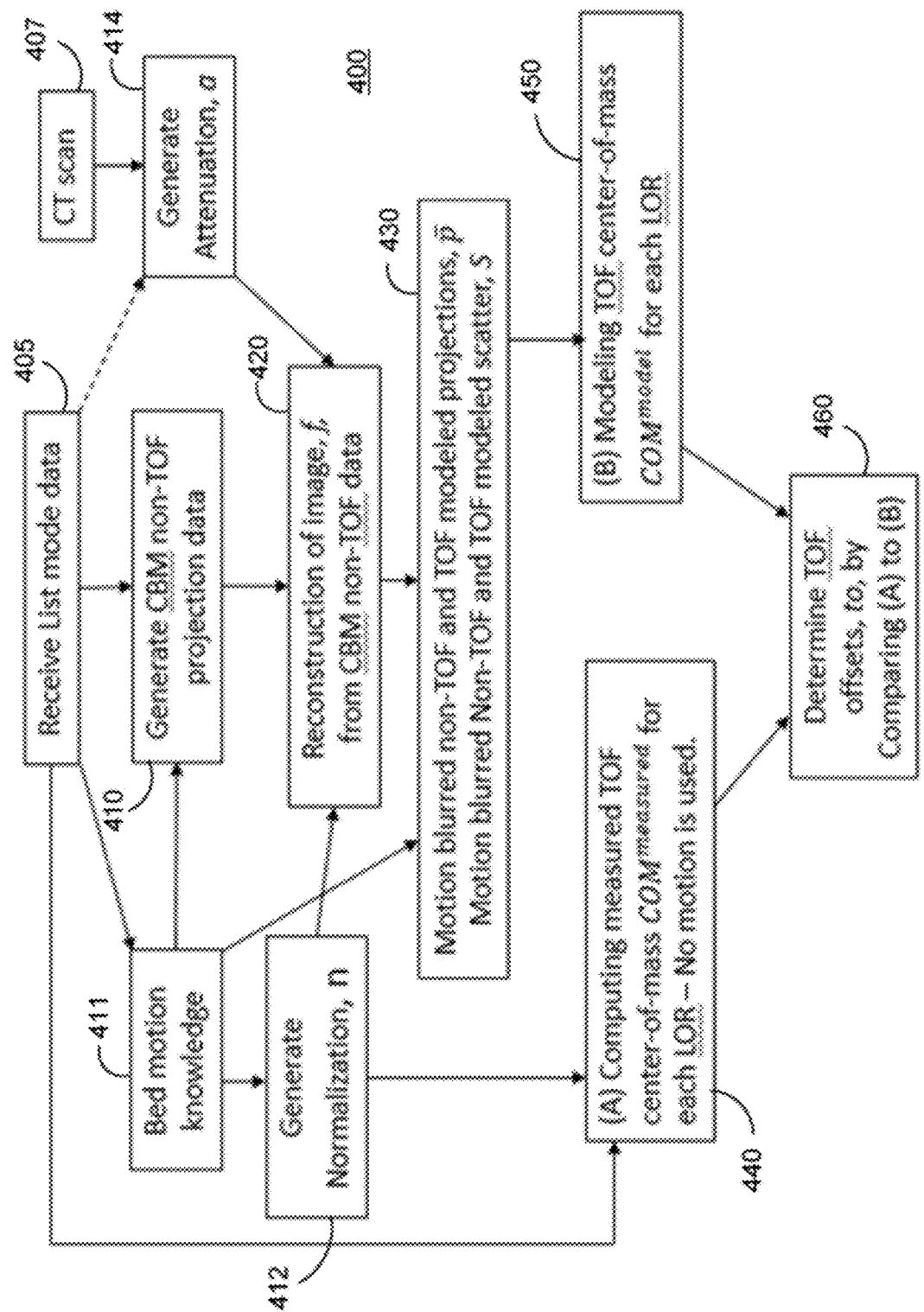
FIG. 3B is a flowchart 400 illustrating the TA procedure of the present disclosure for a CBM mode PET scanner.

FIG. 3B is a flowchart 400 illustrating the TA procedure of the present disclosure in a CBM system, performed by the TA manager 135. Referring to the flowchart 400, in some embodiments, the system's TA manager receives list mode data from PET scan of an axially short cylinder phantom (box 405). The emission data used does not require a CT scan of the cylinder phantom. With the list mode data, CBM non-TOF projection data is generated (box 410) utilizing the CBM bed motion knowledge (box 411). The bed motion data is stored in the list mode data file and is reported with a fraction of a second interval with a precision of a fraction of a millimeter. This provides the bed motion knowledge. The CBM data generation is a dynamic process of assignment list mode events into proper sonogram planes. The list mode events histogramming into CBM sonogram space utilize the nearest neighbor interpolation in the axial direction. In other words, when the CBM bed is shifted by a distance equal to that of the separation between sonogram planes, the event from the same detector pair will be assigned to the next image data plane. The normalization array n is also generated (box 412) utilizing the CBM bed motion knowledge (box 411). The normalization array n is computed by simulating the movement of an object through the scanner, assisted by the monitoring of basic scanner acquisition parameters such as the singles rate. The procedure is basically scanner normalization coefficients averaging specifically for every sinogram plane. The attenuation factor a is also generated from the list mode data (box 414). One of ordinary skill in the art of medical imaging technology would readily understand how to generate these from the list mode data.

The flowchart 400 also covers another option for attenuation correction, where the attenuation factor a is obtained from a CT scan of an axially short phantom (box 407).

Next, image f is reconstructed from the CBM non-TOF projection data (box 420), corrected for scanner efficiency by the normalization array n, and for attenuation by the attenuation factor a. Knowing f, in step 430, motion blurred non-TOF and TOF scatter S and motion blurred non-TOF and TOF projections $\bar{p}$ are modeled. The motion blurring referenced here is attributed to the bed motion in CBM mode. It will be noted here that f, n, a, S, and $\bar{p}$ are vectors as they would be readily understood by those of ordinary skill in the art of medical imaging technology.

The process of reconstructing the image f from the CBM non-TOF projection data referenced in box 420 is known by those skilled in the art. An example of such process can be found in V. Y. Panin, et al., *Continuous Bed Motion on clinical scanner: design, data correction, and reconstruction*, Phys. Med. Biol. 59 (2014) 6153-6174, the entire contents of which are incorporated herein by reference.

Then in step 450, for each LOR, TOF center-of-mass (COM) data, $COM_{\rho\theta\zeta}^{model}$, of true coincidence distribution acquired in a stationary system of coordinates is estimated by modeling from zero order and first order moments $\overline{M}_0$, $\overline{M}_1$ of the modeled TOF data $\bar{p}_{\rho\theta\zeta T}$. This is carried out using the equation group (7) discussed above:

$$COM_{\rho\theta\zeta}^{model} = \frac{\overline{M}_1(\rho\theta\zeta)}{\overline{M}_0(\rho\theta\zeta)},$$

where $$\overline{M}_1(\rho\theta\zeta) = \sum_T T\bar{p}_{\rho\theta\zeta T}, \overline{M}_0(\rho\theta\zeta) = \sum_T \bar{p}_{\rho\theta\zeta T}, \text{ and}$$

$$\text{and } \bar{p}_{\rho\theta z T} = B\left(a_{\rho\theta\zeta}\sum_k C_{\rho\theta\zeta T,k} f_k + S_{\rho\theta\zeta T}\right).$$

As with the stationary bed mode calculations discussed above, note that normalization is not needed (canceled over the numerator and denominator) in the COM estimation per each LOR. Note that $M_0$ is independent of time resolution model. Meaning that $M_0$ will stay same for any resolution of scanner, e.g. 250 or 500 ps. Moreover, if in reality TOF profile was not Gaussian, but other symmetrical profile, $M_0$ will still be the same value. $M_1$ is also independent of time resolution model in true unscattered part, assuming normalized symmetrical TOF kernel. This can be an important advantage of this inventive method, since uniform (across various LORs) time resolution cannot be guaranteed and its exact knowledge may not be necessary.

In list mode processing, represented by step 440, measured TOF COM, $COM^{measured}$, is computed for each LOR as well using the following expression group (3):

$$COM_{\rho\theta\zeta}^{measured} = \frac{n_{\rho\theta\zeta}M_1(\rho\theta\zeta)}{\overline{M}_0(\rho\theta\zeta)},$$

where $COM_{\rho\theta\zeta}^{measured}$ is the measured TOF COM, and $$M_1(\rho\theta\zeta) = \sum_T T(y_{\rho\theta\zeta T} - r_{\rho\theta\zeta T}).$$

Note that the total mass $M_0$ in the denominator is computed by using modeled data instead of measured data to suppress noise magnification by division. LOR normalization (which is normalization coefficient computed for every LOR individually) is used on measured data. In previous notation, sinograms are compressed data, which is projection bin containing more than one LOR. Consequently, normalization is combined over LORs for sonogram data. Projection data of list mode are not compressed, each bin contain one LOR. Computation of $M_1$ involves subtraction of delayed event r and summation of prompt event y.

In step 460, as in the stationary bed case, the TOF time offsets, to, is determined. This is accomplished by first taking the difference, $\Delta_{\rho\theta\zeta}$, between the measured TOF COM, $COM_{\rho\theta\zeta}^{measured}$, from expressions (3) and the modeled TOF COM, $COM_{\rho\theta\zeta}^{model}$, mean values from expressions (7): $\Delta_{\rho\theta\zeta} = COM_{\rho\theta\zeta}^{measured} - COM_{\rho\theta\zeta}^{model}$.

$\Delta_{\rho\theta\zeta}$ is defined by individual detector crystals, denoted by indices i and j, and TO is denoted by to. An unweighted Gaussian model (4) discussed above is used in the optimization procedure to estimate the TOs.

Time Alignment

System TA procedure produces TO estimation which is stored in the system and applied at coincidence processor level. This results in the list mode file containing correct timing information (i.e. adjusted for the TO) for every coincidence photon pair. System TA procedure is not frequently executed.

TA procedure is the same as described above in TO estimation and CBM acquisition case except that it estimates TOs for a particular data set and TO estimations are taking into account during additional rebinning of the list mode data. In other words, TA procedure detects residual TOs with respect to TO estimation, stored on the system. Only rebinned data will contain correct timing information.

According to another aspect of the present disclosure, a non-transitory, machine-readable storage medium encoded with program instructions for controlling the PET scanner system 100 is disclosed. When a processor in the TA manager 135 of the PET scanner system executes the program instructions, the processor performs a method for TA of the PET scanner, where the method comprises:
 (a) receiving list mode data from PET scan of an axially short phantom in CBM mode;
 (b) generating non-time of flight (TOF) projection data, scanner efficiency normalization array n, and attenuation factor a;
 (c) reconstructing image f from the non-TOF projection data, corrected for scanner efficiency by a normalization array n, and for attenuation by attenuation factor a;
 (d) modeling non-TOF and TOF scatter S and non-TOF and TOF projections $\bar{p}$;
 (e) for each line of response, estimating by modeling TOF center-of-mass (COM) of true coincidence distribution from zero order and first order moments $M_0$ and $M_1$ of the modeled TOF data;
 (f) for each line of response, computing measured TOF COM; and
 (g) determining TOF time offsets, to, by taking the difference between the measured TOF COM and the modeled TOF COM.

In the present disclosure when estimation of certain parameters or values are accomplished by modeling, the terms "estimating" and "modeling" are used interchangeably to mean the same thing.

In some embodiments of the non-transitory, machine-readable storage medium, the step (e) is carried out using the following expressions:

$$COM_{\rho\theta\zeta}^{model} = \frac{\overline{M}_1(\rho\theta\zeta)}{\overline{M}_0(\rho\theta\zeta)};$$

wherein $$\overline{M}_1(\rho\theta\zeta) = \sum_T T\bar{p}_{\rho\theta\zeta T}, \overline{M}_0(\rho\theta\zeta) = \sum_T \bar{p}_{\rho\theta\zeta T}; \text{ and}$$

$$\bar{p}_{\rho\theta\zeta T} = a_{\rho\theta\zeta} \sum_k C_{\rho\theta\zeta T,k} f_k + S_{\rho\theta\zeta T};$$

wherein $(\rho,\theta,\zeta)$ is spatial projection index representing radial $(\rho)$, azimuthal $(\theta)$, and axial $(\zeta)$ projections, which includes polar angle segments;

wherein T is TOF bin index;

wherein $COM_{\rho\theta\zeta}^{model}$ is the estimated TOF COM data, $\bar{p}_{\rho\theta\zeta T}$ is the modeled wherein TOF data, $\overline{M}_1(\rho\theta\zeta)$ is the first order moment of $\bar{p}_{\rho\theta\zeta T}$, $\overline{M}_0(\rho\theta\zeta)$ is the zero order moment of $\bar{p}_{\rho\theta\zeta T}$, and C is the geometrical projection system matrix.

In some embodiments of the non-transitory, machine-readable storage medium, the step (f) is carried out using the following expressions:

$$COM_{\rho\theta\zeta}^{measured} = \frac{n_{\rho\theta\zeta}M_1(\rho\theta\zeta)}{\overline{M}_0(\rho\theta\zeta)},$$

wherein $COM_{\rho\theta\zeta}^{measured}$ is the measured TOF COM and $$M_1(\rho\theta\zeta) = \sum_T T(y_{\rho\theta\zeta T} - r_{\rho\theta\zeta T}).$$

According to another aspect, a non-transitory, machine-readable storage medium encoded with program instructions for controlling a CBM PET scanner is disclosed. When a processor in the TA manager 135 of the CBM PET scanner system 100 executes the program instructions, the processor performs a method for time alignment of the CBM PET scanner, where the method comprises:
 (a) receiving list mode data from PET scan of an axially short phantom in CBM mode;
 (b) generating CBM non-time of flight (TOF) projection data, scanner efficiency normalization array n, and attenuation factor a;
 (c) reconstructing image f from the CBM non-TOF projection data, corrected for scanner efficiency by the normalization array n, and for attenuation by the attenuation factor a;
 (d) modeling motion blurred non-TOF and TOF scatter S and motion blurred non-TOF and TOF projections $\bar{p}$;
 (e) for each line of response, estimating TOF center-of-mass (COM) of true coincidence distribution acquired in a stationary system of coordinates from zero order and first order moments $\overline{M}_0$ and $\overline{M}_1$ of the modeled TOF data;
 (f) for each line of response, computing measured TOF COM; and
 (g) determining TOF time offsets, to, by taking the difference between the measured TOF COM and the modeled TOF COM.

In some embodiments of the non-transitory, machine-readable storage medium, the step (e) is carried out using the following expressions:

$$COM_{\rho\theta\zeta}^{model} = \frac{\overline{M}_1(\rho\theta\zeta)}{\overline{M}_0(\rho\theta\zeta)};$$

wherein $$\overline{M}_1(\rho\theta\zeta) = \sum_T T\bar{p}_{\rho\theta\zeta T}, \overline{M}_0(\rho\theta\zeta) = \sum_T \bar{p}_{\rho\theta\zeta T}; \text{ and}$$

-continued $$\overline{p}_{\rho\theta zT} = B\left(a_{\rho\theta\zeta}\sum_k C_{\rho\theta\zeta T,k} f_k + S_{\rho\theta\zeta T}\right);$$

wherein (ρ,θ,ζ) is spatial projection index representing radial (ρ), azimuthal (θ), and axial (ζ) projections, which includes polar angle segments;
wherein T is TOF bin index;
wherein $COM_{\rho\theta\zeta}^{model}$ is the estimated TOF COM data, $\overline{p}_{\rho\theta\zeta T}$ is the modeled TOF data, $\overline{M}_1(\rho\theta\zeta)$ is the first order moment of $\overline{p}_{\rho\theta\zeta T}$, $\overline{M}_0(\rho\theta\zeta)$ is the zero order moment of $\overline{p}_{\rho\theta\zeta T}$, and C is the geometrical projection system matrix; and
and B is a blurring operator defined as $$B(\overline{p}_{\rho\theta\zeta T}) = \int_0^{t'_{acq}} dt' \sum_\zeta e^{-\lambda t} d_{\rho\theta z}(t) \overline{p}_{\rho\theta\zeta T} \delta_{z,Z(\zeta,t)}.$$

In some embodiments of the non-transitory, machine-readable storage medium, the step (f) is carried out using the following expressions:

$$COM_{\rho\theta\zeta}^{measured} = \frac{n_{\rho\theta\zeta} M_1(\rho\theta\zeta)}{\overline{M}_0(\rho\theta\zeta)},$$

wherein $COM_{\rho\theta\zeta}^{measured}$ is the measured TOF COM and $$M_1(\rho\theta\zeta) = \sum_T T(y_{\rho\theta\zeta T} - r_{\rho\theta\zeta T}).$$

CE Normalization Estimation

According to another aspect, a method for scanner performance monitoring (i.e. scanner calibration) for CBM acquisition mode using axially short phantom is disclosed. CBM data formation, counts from the various detector pairs are combined together taking into account the axial bed motion. While it is beneficial for activity reconstruction, axial CE structure is practically lost in corresponding computed normalization array due to averaging over the axial bed motion. As done in the step-and-shoot (S&S) stationary acquisition disclosed in U.S. patent application publication No. 2015/0297168, additional complementary data is generated during the CBM acquisition mode scan of the axially short phantom.

In the complementary data set, activity from TOF data of the axially short phantom is integrated over the axial motion of the patient bed, however CE structure is preserved. The same rebinner can be used to generate both data sets. Using two complementary data sets, simultaneous reconstruction of activity and scintillation CE normalization component from axially short phantom TOF data from the CBM acquisition process becomes practical. The algorithm can be interpreted as regular activity maximum likelihood (ML) reconstruction with nested loop of scintillation CE normalization component estimation, which uses the same data which are compressed differently.

By taking into consideration the axially short phantom TOF data integrated over the CBM acquisition motion, an estimation can be made of the CBM acquired axially short phantom image as well as the scintillation CE normalization coefficient. The CE normalization estimation procedure discussed herein is similar to the one disclosed in U.S. Pat. No. 10,482,596, that is generalized for using patient scan data in CBM acquisition mode. The disclosure of U.S. Pat. No. 10,482,596 is incorporated herein by reference. However, here CBM scan data of an axially short phantom is used to generate accurate CE normalization estimate.

Only CE normalization component needs to be estimated. This further significantly reduces the number of unknowns and solution sensitivity to noise, but requires development of specific reconstruction algorithms. The ML reconstruction of activity and crystal efficiency (A-CE) problem has additional aspects: the scattering event modeling takes part in the efficiencies estimation, and the model equations are non-linear with respect to scintillation CE with the known activity. What is attenuation and activity are defined up to scaling constant, since only their product is used in estimation. Thus, unknown global scaling is a lesser problem, since the average efficiency value is known due to the separate calibration of voxel activity to injected dose of the radioactive tracer.

The central controller 28 operates pursuant to stored instructions to perform various acts described herein, such as determining decay correction efficiency, determining a singles rate for a given time, determining detection time efficiency, calculating the normalization coefficients, normalizing the line-of-response data, and/or reconstruction. The central controller 28 is configured by software and/or hardware to perform any or all of the acts of the methods disclosed herein.

Figure 5:
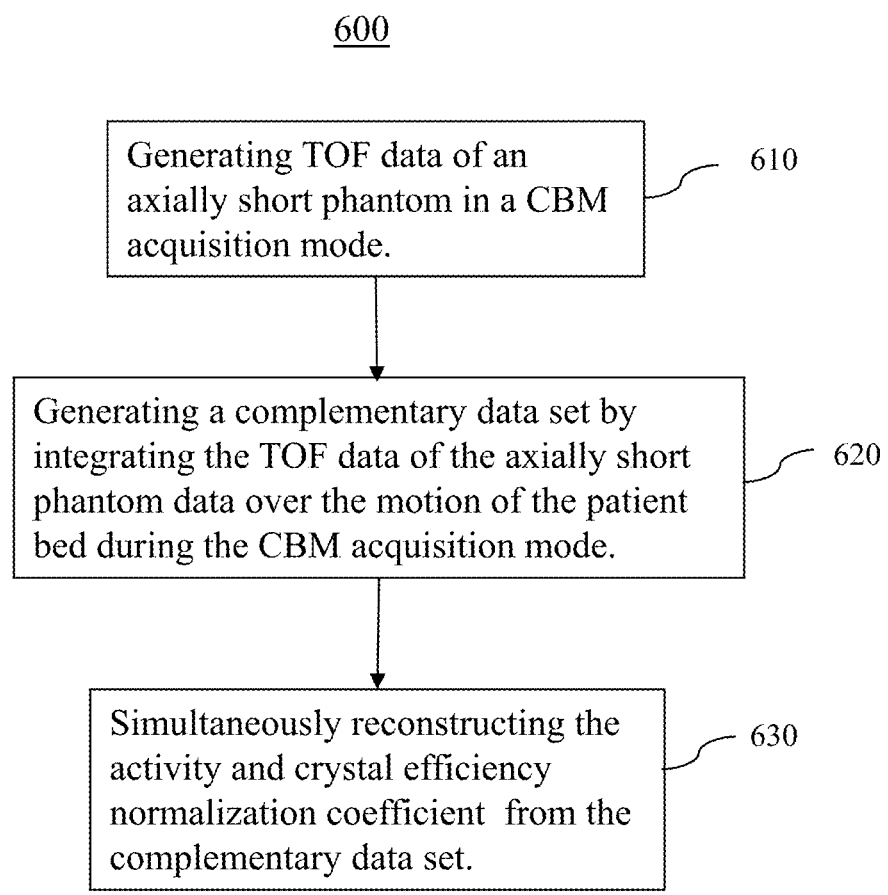
FIG. 5 is a flowchart 600 illustrating a method for generating CE normalization estimation for a PET scanner by CBM scanning an axially short cylinder phantom 60 according to some embodiments of the present disclosure.
Figure 7A:
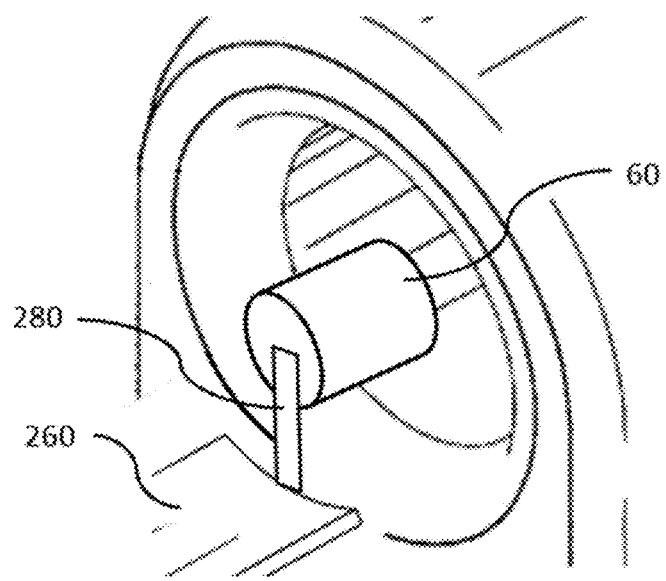
FIG. 7A shows an example of an axially short cylinder phantom placed on a standard holder mounted on a CBM bed according to the present disclosure.

FIG. 5 is a flowchart 600 illustrating a method for generating CE normalization estimation for a PET scanner by CBM scanning an axially short cylinder phantom 60 according to some embodiments of the present disclosure. The axially short cylinder phantom 60 is mounted on the patient bed 206 that moves the phantom during the CBM acquisition of the phantom 60 as shown in FIG. 7A. The method comprises (a) generating TOF data of the axially short cylinder phantom 60 in a CBM acquisition mode, while accounting for the axial motion of the patient bed 206 during the CBM acquisition, as a first data set (see Box 610); (b) generating a complementary data set by integrating the TOF data of the axially short cylinder phantom 60 over the axial motion of the patient bed 206 during the CBM acquisition (see Box 620); and (c) simultaneously reconstructing the activity and CE normalization coefficient from the complementary data set (see Box 630).

The operation and configuration of the central controller 28 is first described in general below. One example implementation is described in more detail in the following discussion.

The central controller 28 is configured to determine normalization coefficients. The weighting to account for differences in efficiency for detecting different lines of response relative to the patient is calculated. In CBM, the lines-of-response change axial position over time when considered relative to the patient. As a result, various detector pairs and other factors contribute to the efficiency of detection. These factors, which may vary over time, are included in the computation of the normalization coefficients.

The central controller 28 accounts for the decay. A decay correction efficiency is determined for an isotope used during the PET scan. The isotope's decay characteristic changes over time. This variation in decay is used for the decay correction efficiency.

The central controller 28 accounts for the velocity variation of the bed and patient. As the velocity of the bed changes, the detection time efficiency changes. The detection time efficiency at different times and corresponding positions of the bed or patient during the PET scan is determined based, in part, on the velocity.

The central controller 28 may account for other factors as well, such as the time variation of the singles rate and/or normalization of the scanner (e.g., normalization used in S&S or other scanning protocols without the axial bed motion during the scan).

The central controller 28 applies the normalization coefficients. For each given LOR, the activity is weighted by the normalization coefficient for that LOR. The central controller 28 or another processor may reconstruct the object space from the normalized LOR.

The central controller 28 uses the events (e.g., line-of-response events), empirical information (e.g., global singles rate), and/or known information (e.g., decay correction constant) stored in the memory 26 for processing. For processing, the data bypasses the memory 26, is temporarily stored in the memory 26, or is loaded from the memory 26.

The detected events, LOR information (e.g., sinograms), time step, singles rate, decay information, scanner normalization information, CBM normalization coefficients, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 100 or a remote workstation or database, such as a PACS memory.

The memory 26 is additionally or alternatively a non-transitory computer readable storage medium with processing instructions. The memory 26 stores data representing instructions executable by the programmed central controller 28 for computing normalization coefficients in continuous bed motion acquisition. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 100 may include a display. For example, the central controller 28 reconstructs the patient or object being scanned from the normalized line-of-response data. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

CBM Data Rebinning

The method for scanner performance monitoring during a QC scanning of an axially short phantom by CBM acquisition according to an aspect of the present disclosure involves CBM Data Rebinning. As mentioned in connection with FIGS. 4A and 4B above, there are two systems of coordinates in CBM acquisition. One is laboratory, which is aligned with a scanner. The second is moving, where the object is stationary. The CBM scanner data are represented by transaxial radial coordinate $\rho$, azimuthal coordinate $\theta$, and axial plane coordinate z, which includes a polar angle. The moving object virtual LORs have the same transaxial coordinates, but are described by different axial coordinate $\zeta$. Let us denote a function in which we map coordinate $\zeta$ onto the scanner system coordinate as $Z(\zeta,t)$. This function uses object/bed axial motion knowledge. The function aligns laboratory and moving system axial coordinates with the nearest neighbor approximation in order to preserve Poisson statistics during data rebinning. The rebinner produces two types of data: one data set for A (activity reconstruction) and a complimentary data set for CE estimations.

Activity Reconstruction Step

TOF prompt CBM data y with spatial projection index $j=(\rho, \theta, \zeta)$ and TOF bin index T can be modeled by combining the true events (unscattered gamma coincidence events) modeled projection $\bar{p}$ from the emission object f, defined by voxel index k, corrected for scanner efficiency through a normalization array n for attenuation by a, and scatter estimation S, corrected for scanner efficiency as well, and mean random data $\bar{r}$:

$$\bar{y}_{\rho\theta\zeta T} = a_{\rho\theta\zeta} n^{-1}_{\rho\theta\zeta}(\varepsilon) \sum_k C_{\rho\theta\zeta T,k} f_k + n^{-1}_{\rho\theta z} S_{\rho\theta\zeta T} + \bar{r}_{\rho\theta\zeta T} = \quad (1)$$

$$a_{\rho\theta\zeta} n^{-1}_{\rho\theta\zeta}(\varepsilon) \bar{p}_{\rho\theta\zeta T} + n^{-1}_{\rho\theta z} S_{\rho\theta\zeta T} + \bar{r}_{\rho\theta\zeta T}$$

where C is the geometrical projection system matrix, which contains probabilities to detect coincidence event at $(\rho, \theta, \zeta)$ originated at activity array voxel k, and $\varepsilon$ is the crystal efficiency. The CBM data normalization (denoted by coordinate $\zeta$) is computed (integrated over time) from scanner normalization factors accounting for the axial movement during CBM according to:

$$n^{-1}_{\rho\theta\zeta} = \int_0^{t_{acq}} dt \sum_z e^{-\lambda t} d_{\rho\theta z}(t) n^{-1}_{\rho\theta z} \delta_{z,Z(\zeta,t)} \quad (2)$$

where $\lambda$ is the decay correction constant for a specific isotope, $\delta$ is Kronecker's delta, d is the dead time correction factor, and $t_{acq}$ is CBM acquisition time. Dead time correction, which accommodates for signal loss when detector processes relatively high count rate, is time dependent due to the variable single rate. Equation (2) describes the averaging process of virtual LOR efficiency over scanner LOR efficiencies and is discussed in more detail by the inventor in V. Y. Panin, A. M. Smith, J. Hu, F. Kehren and M. E. Casey, "Continuous bed motion on clinical scanner: Design, Data Correction and Reconstruction", *Phys. Med. Bio.*, vol. 59, pp. 6153-6174, 2014.

The scanner normalization factors (denoted by coordinate z) may accommodate for the mashing and rebinning of the LORs, as with Siemens scanners, connecting two detector crystals i and i' into projection bin:

$$n_{\rho\theta z}^{-1}(\varepsilon) = \sum_{i,i'} \omega_{\rho\theta z,ii'} g_{ii'} \varepsilon_i \varepsilon_{i'}, \quad (3)$$

where g is the geometrical component of the normalization array. The ω is the LOR contribution factor into projection data due to mashing and spanning data compression techniques, where ω is defined by the following:

$$\omega_{j,ii'} = \begin{cases} 1/2, & \text{if } ii' \text{ contribute to sinogram bin } j \\ 0, & \text{otherwise} \end{cases} \quad (4)$$

Due to integration over axial movement in (2), the CBM normalization array loses information about the axial CE structure. Therefore, the described data set is used for activity reconstruction, assuming known CEs.

CE Estimation Step (the CE-Step)

The complementary data set, acquired in a stationary system of coordinate, prompt data, is modeled as follows:

$$\bar{y}_{\rho\theta zT} = n_{\rho\theta z}^{-1}(\varepsilon) B \left( a_{\rho\theta\zeta} \sum_k C_{\rho\theta\zeta T,k} f_k \right) + n_{\rho\theta z}^{-1}(\varepsilon) B(S_{\rho\theta\zeta T}) + \bar{r}_{\rho\theta zT} = \quad (5)$$

$$n_{\rho\theta z}^{-1}(\varepsilon) \bar{p}_{\rho\theta zT} + n_{\rho\theta z}^{-1}(\varepsilon) S_{\rho\theta zT} + \bar{r}_{\rho\theta zT},$$

where the motion blurring operator $y_{\rho\theta z}$ can be denoted as $$y_{\rho\theta z} = B(y_{\rho\theta\zeta}) = \int_0^{t'_{acq}} dt' \sum_\zeta e^{-\lambda t} d_{\rho\theta z}(t) y_{\rho\theta\zeta} \delta_{z,Z(\zeta,t)}. \quad (6)$$

Note that the definition of the CE-step modeled true $\bar{p}$ includes attenuation in the blurring operation. Due to integration over movement in (6), the axial structure of the activity distribution will be lost.

The total acquisition time can be different between (2) and (6), since modeling in (5) should not include projection outside the axial range of the reconstructed activity field-of-view (FOV). Random means are different between the two data sets as well and are estimated differently from delay events.

ML-ACE Algorithm

Figure 6:
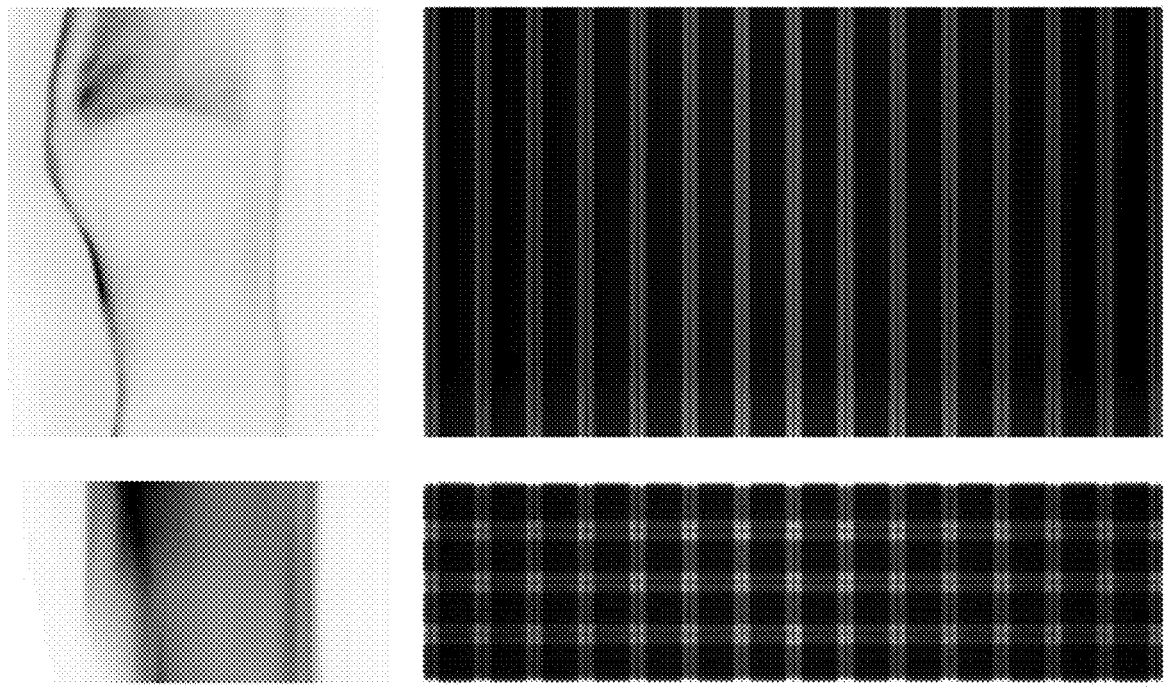
FIG. 6 shows data sets used in ML-ACE algorithm steps.

Simultaneous activity and crystal efficiency normalization component reconstruction (A-CE) can be carried out using the two data sets shown in FIG. 6. In FIG. 6, the first column represents modeled activity projection. The second column represents normalization array, direct planes. The first row is the activity reconstruction step (A-step) and the second row is the CE normalization component reconstruction step (CE-step). Vertical axis is axial direction. The optimization is performed by iterations; each is divided into the two steps described above. The A-step is the activity update with the fixed normalization (efficiencies) array, where CBM TOF data are used. A commonly used ordered subsets expectation maximization (OS-EM) algorithm. The following objective function $$L_A(f) = \sum_{j=\{\rho\theta\zeta\},T} (y_{jT} \ln(\bar{y}_{jT}) - \bar{y}_{jT})$$

is to be maximized w.r.t. f, where f is activity image as defined in (1).

The CE-step is the efficiencies updated by the iterative algorithm described in V. Y. Panin, "Monotonic Iterative Algorithms for Crystal Efficiencies Estimation from Normalization Data and Single Rates Estimation from Compressed Random Coincidence Data," 2013 *IEEE Nucl. Sci. Symp. and Med. Imag. Conf.* (*Seoul, Korea*), M23-1, 2013, where the motion blurred activity and scatter distributions will be known from the A-step. In this step, complimentary TOF or non-TOF data are used and four iterations are performed in the estimation of CE. Here, the goal is maximization of the following objective function:

$$L_{CE}(\varepsilon) = \sum_{j=\{\rho\theta z\},T} (y_{jT} \ln(\bar{y}_{jT}) - \bar{y}_{jT}) \text{ w.r.t. } \varepsilon.$$

The CE-step updated equations are provided for completeness:

$$\varepsilon_i^{(m+1)} = \frac{-B_i + \sqrt{B_i^2 + 4A_i C_i}}{2A_i} \quad (7)$$

$$A_i = \sum_j \sum_{i'} \omega_{j,ii'} g_{ii'} (\bar{p}_j(f) + S_j),$$

$$B_i = \sum_j \sum_{i'} \omega_{j,ii'} (\bar{p}_j(f) + S_j) \varepsilon_{i'}^{(m)} - A_i \varepsilon_i^{(m)}$$

$$C_i = \varepsilon_i^{(m)} \sum_{jT} \frac{y_{jt}}{\bar{y}_{jT}^{(m)}(f, \varepsilon^{(m)})} \sum_{i'} \omega_{j,ii'} (\bar{p}_{jT}(f) + S_{jT}) \varepsilon_{i'}^{(m)}$$

$$j = \{\rho\theta z\}$$

where m is the iteration number for the updating the crystal efficiency ε. Note that TOF information was eliminated in the computing of A and B, where $\bar{p}_j$ and $S_j$ represent summation of $\bar{p}_{jT}$ and $S_{jT}$ over TOF bin index T. However, TOF information is preserved in the computing of C. If non-TOF data are used in the CE-step, then the computing of C has no summation over the T index.

Each step uses a simultaneous monotonic update algorithm. The two steps together, however, can represent the sequential update method. The method can be interpreted as regular activity ML reconstruction with a nested loop of CE normalization component estimation, which uses effectively the same data yet is compressed differently. In the following TOF/non-TOF nested loop, ML-ACE will denote CE normalization component estimations from TOF/non-TOF CE-step data.

The ML-ACE initial condition was CE initiated by the average block values and uniform activity distribution. Three iterations of the sequential update method were performed. This effectively resulted in three iterations and 21 subsets of OS-EM activity reconstruction and 12 iterations of CE normalization component estimation.

Figure 12:
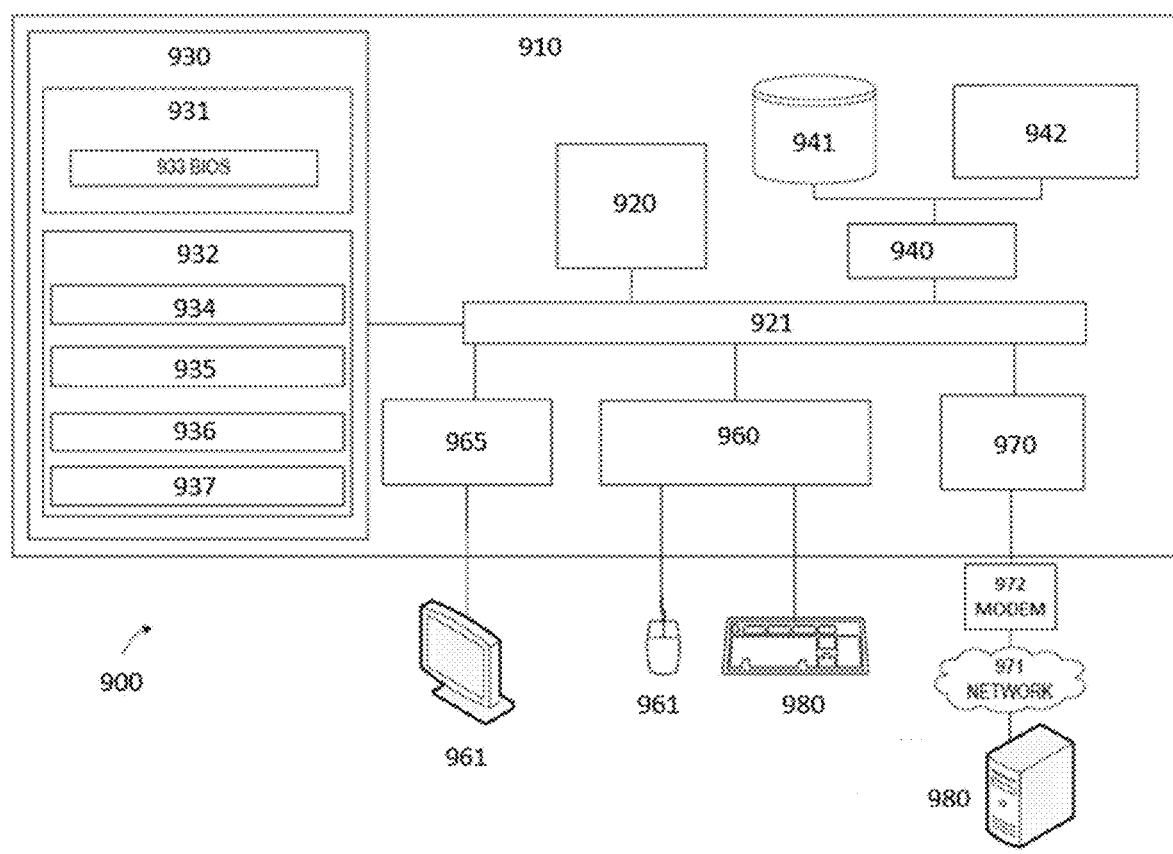
FIG. 12 is a detailed block diagram of an example of the computer system suitable for the system of FIG. 1, according to some embodiments.

FIG. 12 illustrates an exemplary computing environment 900 within which includes an embodiments of the central controller 28 of FIG. 1. For example, computing environment 900 can be used to implement the method disclosed herein. Computers and computing environments, such as central controller 28 and computing environment 900, are known to those of skill in the art and thus are described briefly here.

As shown in FIG. 12, the central controller 28 can include a communication mechanism such as a system bus 921 or other communication mechanism for communicating information within the central controller 28. The central controller 28 further includes one or more processors 920 coupled with the system bus 921 for processing the information.

The processors 920 can include one or more central processing units (CPUs), graphical processing units (GPUs), or any other processor known in the art. More generally, a processor can include a device for executing machine-readable instructions stored on a computer readable medium, for performing tasks and can comprise any one or combination of, hardware and firmware. A processor can also comprise memory storing machine-readable instructions executable for performing tasks. A processor acts upon information by manipulating, analyzing, modifying, converting or transmitting information for use by an executable procedure or an information device, and/or by routing the information to an output device. A processor can use or comprise the capabilities of a computer, controller or microprocessor, for example, and be conditioned using executable instructions to perform special purpose functions not performed by a general purpose computer. A processor can be coupled (electrically and/or as comprising executable components) with any other processor enabling interaction and/or communication there-between. A user interface processor or generator can include electronic circuitry or software or a combination of both for generating display images or portions thereof. A user interface can comprise one or more display images enabling user interaction with a processor or other device Continuing with reference to FIG. 12, the central controller 28 also includes a system memory 930 coupled to the system bus 921 for storing information and instructions to be executed by processors 920. The system memory 930 can include computer readable storage media in the form of volatile and/or nonvolatile memory, such as read only memory (ROM) 931 and/or random access memory (RAM) 932. The RAM 932 can include other dynamic storage device(s) (e.g., dynamic RAM, static RAM, and synchronous DRAM). The ROM 931 can include other static storage device(s) (e.g., programmable ROM, erasable PROM, and electrically erasable PROM). In addition, the system memory 930 can be used for storing temporary variables or other intermediate information during the execution of instructions by the processors 920. A basic input/output system 933 (BIOS) containing the basic routines that help to transfer information between elements within central controller 28, such as during start-up, can be stored in the ROM 931. RAM 932 can contain data and/or program modules that are immediately accessible to and/or presently being operated on by the processors 920. System memory 930 can additionally include, for example, operating system 934, application programs 935, other program modules 936 and program data 937.

The central controller 28 can also include a disk controller 940 coupled to the system bus 921 to control one or more storage devices for storing information and instructions, such as a magnetic hard disk 941 and a removable media drive 942 (e.g., floppy disk drive, compact disc drive, tape drive, and/or solid state drive). Storage devices can be added to the central controller 28 using an appropriate device interface (e.g., a small computer system interface (SCSI), integrated device electronics (IDE), Universal Serial Bus (USB), or Fire Wire).

The central controller 28 can also include a display controller 965 coupled to the system bus 921 to control a display or monitor 966, such as a liquid crystal display (LCD), for displaying information to a computer user. The computer system includes an input interface 960 and one or more input devices, such as a keyboard 962 and a pointing device 961, for interacting with a computer user and providing information to the processors 920. The pointing device 961, for example, can be a mouse, a light pen, a trackball, or a joy stick for communicating direction information and command selections to the processors 920 and for controlling cursor movement on the display 966. The display 966 can provide a touch screen interface which allows input to supplement or replace the communication of direction information and command selections by the pointing device 961.

The central controller 28 can perform a portion or all of the processing steps of embodiments in response to the processors 920 executing one or more sequences of one or more instructions contained in a memory, such as the system memory 930. Such instructions can be read into the system memory 930 from another computer readable medium, such as a magnetic hard disk 941 or a removable media drive 942. The magnetic hard disk 941 can contain one or more data stores and data files used by various embodiments. Data store contents and data files can be encrypted to improve security. The processors 920 can also be employed in a multi-processing arrangement to execute the one or more sequences of instructions contained in system memory 930. In alternative embodiments, hard-wired circuitry can be used in place of or in combination with software instructions. Thus, embodiments are not limited to any specific combination of hardware circuitry and software.

Some embodiments include software instructions written in a high level language, such as C, C++, C #, Java, Fortran or Python. Some embodiments are written for a multi-paradigm numerical computing environment, such as Matlab, sold by Mathworks, Inc. of Natick, Massachusetts, or the like.

As stated above, the central controller 28 can include at least one computer readable medium or memory for holding instructions and for containing data structures, tables, records, or other data described herein. The term "computer readable medium" as used herein refers to any non-transitory machine-readable storage medium that participates in providing instructions to the processors 920 for execution. A computer readable medium can take many forms including, but not limited to, non-transitory, non-volatile media and volatile media. Non-limiting examples of non-volatile media include optical disks, solid state drives, magnetic disks, and magneto-optical disks, such as magnetic hard disk 941 or removable media drive 942. Non-limiting examples of volatile media include dynamic memory, such as dynamic random access memory 930.

The central controller 28 can operate in a networked environment using logical connections to one or more remote computers, such as remote computing device 980. Remote computing device 980 can be a personal computer (laptop or desktop), a mobile device, a server, a router, a network PC, a peer device or other common network node, and typically includes many or all of the elements described above relative to central controller 28. When used in a networking environment, central controller 28 can include modem 972 for establishing communications over a network 971, such as the Internet. Modem 972 can be connected to system bus 921 via user network interface 970, or via another appropriate mechanism.

Network 971 can include, but is not limited to, the Internet, an intranet, a local area network (LAN), a wide area network (WAN), a metropolitan area network (MAN), a personal area network (PAN) a direct connection or series of connections, a cellular telephone network, or any other network or medium capable of facilitating communication between central controller 28 and other computers (e.g., remote computing device 980). The network 971 can be wired, wireless or a combination thereof. Wired connections can be implemented using Ethernet, Universal Serial Bus (USB), RJ-6, or any other wired connection. Wireless connections can be implemented using Wi-Fi, WiMAX, and Bluetooth, infrared, cellular networks, satellite or any other wireless connection methodology. Additionally, several networks can work alone or in communication with each other to facilitate communication in the network 971.

The functions and process steps described herein can be performed automatically or wholly or partially in response to user command. An activity (including a step) performed automatically is performed in response to one or more executable instructions or device operation without user direct initiation of the activity.

The methods and system described herein can be at least partially embodied in the form of computer-implemented processes and apparatus for practicing those processes. The disclosed methods can also be at least partially embodied in the form of tangible, non-transitory machine readable storage media encoded with computer program code. The media can include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods can also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods can alternatively be at least partially embodied in a digital signal processor formed of application specific integrated circuits for performing the methods.

Therefore, according to an aspect of the present disclosure, a non-transitory, machine readable storage medium encoded with computer program software is disclosed, such that when a processor executes the computer program software, the processor performs a method for TA in CBM PET scanner, where the method comprises:
- (a) receiving list mode data from PET scan of an axially short phantom in CBM mode;
- (b) generating CBM non-time of flight (TOF) projection data, scanner efficiency normalization array n, and attenuation factor a;
- (c) reconstructing image f from the CBM non-TOF projection data, corrected for scanner efficiency by the normalization array n, and for attenuation by the attenuation factor a;
- (d) modeling motion blurred non-TOF and TOF scatter S and motion blurred non-TOF and TOF projections $\bar{p}$;
- (e) for each line of response, estimating TOF center-of-mass (COM) of true coincidence distribution acquired in a stationary system of coordinates from zero order and first order moments $\overline{M}_0$ and $\overline{M}_1$ of the modeled TOF data;
- (f) for each line of response, computing measured TOF COM; and
- (g) determining TOF time offsets, to, by taking the difference between the measured TOF COM and the modeled TOF COM.

According to some embodiments, a non-transitory, machine readable storage medium encoded with computer program software is disclosed, such that when a processor executes the computer program software, the processor performs a method for monitoring a PET scanner performance during a CBM acquisition is disclosed, wherein the PET scanner has a patient bed that moves an axially short cylinder phantom in an axial motion through the PET scanner during the CBM acquisition, the method comprises:
- (a) generating time-of-flight (TOF) data during the CBM acquisition of the axially short phantom, while accounting for the axial motion of the patient bed during the CBM acquisition, as a first data set;
- (b) generating a complementary data set by integrating the TOF data over the axial motion of the patient bed during the CBM acquisition; and
- (c) simultaneously reconstructing the activity and crystal efficiency normalization coefficient from the complementary data set.

Use of Axially Short Phantom

The "axially short phantom" for the CBM TA procedure and the CE estimation described herein has an axial length that is shorter than the FOV of the PET scanner. The axially short phantom of the present disclosure comprises a cylindrical outer shell that has a conventional length, e.g. about 28 cm long. However, only the central part that is shorter than the FOV of the PET scanner is filled with activity. "Axially short" refers to the fact that the activity filled part of the phantom is shorter than the FOV of the PET scanner. FIG. 7A shows an example of such axially short phantom 600 placed on a standard holder mounted on a CBM bed 260 according to the present disclosure.

Figure 7B:
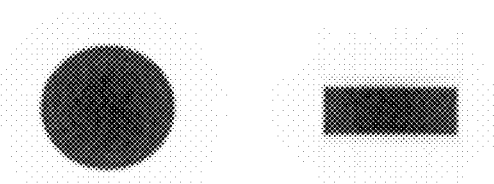
FIG. 7B shows a CBM data reconstruction of activity, transaxial (left) and coronal (right) views.

FIG. 7B shows a CBM data reconstruction of activity, transaxial (left) and coronal (right) views.

Figure 7C:
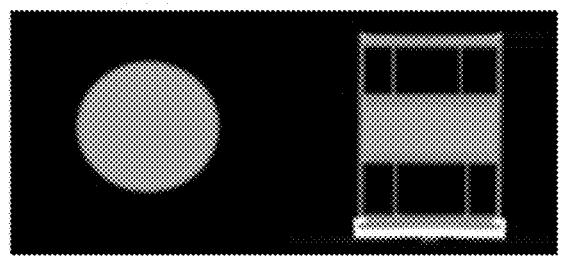
FIG. 7C shows CT based attenuation map, transaxial (left) and coronal (right) views.

FIG. 7C shows CT based attenuation map, transaxial (left) and coronal (right) views.

The rest of the phantom case is filled with air, creating a buffer between the activity filament and the metal holder that attaches the phantom to the CBM bed. The axially short phantom was designed in such a way that the activity LORs do not pass through either the CBM bed or the phantom holder. Compared to a standard conventional length phantom, the axially short phantom disclosed herein is about ¾ lighter and, making it much easier to handle.

Experimental Data for Confirmation

CBM TA procedure was carried out with an axially short phantom and compared to a standard TA procedure carried out with a conventional 28 cm long phantom. The CBM setup with the axially short phantom of the present disclosure was tested on a Siemens Vision PET/CT scanner. There are 760 (trans axial in one ring)×80 (axial rings) detector crystals. The list mode information consists of 13 ps TOF bins. During the TA procedure, the time window is open to 6.7 ns to avoid data truncation in the time direction.

A standard TA procedure was performed using a conventional 28 cm long phantom before acquiring the axially short phantom CBM data for comparison. The list mode scan consisted of 250 million trues counts. The outcome of this procedure is the T0 array, which is downloaded by the firmware for TOF bin index correction in the following list mode data acquisitions of a 4.7 ns time window.

A CBM scan was performed with the axially short phantom, without downloaded estimated TO (no TA), to acquire list mode data. The scan was performed at a speed of 0.3 mm/s. The axially short phantom was completely outside of the scanner FOV at the beginning and at the end of data acquisition scan. This resulted in about 352 million true counts in "stationary" data. Once TOs were estimated, they were applied during list mode data processing by changing the TOF bin indexing. A modified list mode file was used for CE estimation.

For comparison purposes, CBM data were also treated as stationary scans. The bed motion was ignored in order to produce a long virtual cylinder scan (from activity and attenuation point of view). This data set underwent standard procedures for TO and CE estimation.

A line source phantom was placed at the center of scanner to evaluate time resolution according to the National Electrical Manufacturers Association (NEMA) standard. List mode data was acquired without downloading TOs. TOs were applied during list mode data processing by changing TOF bin indexing. In this way, the same data set is used to estimate the performance of various TA procedures.

Figure 8A:
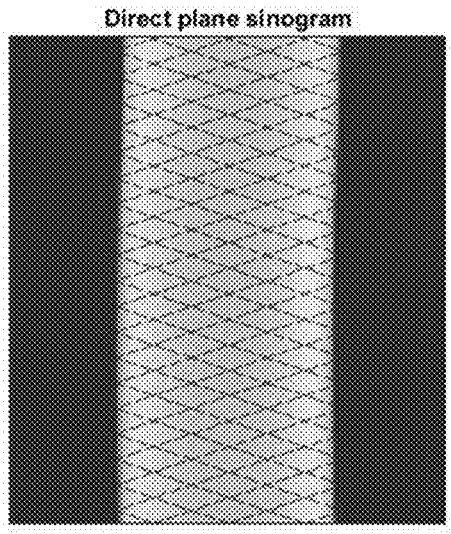
FIGS. 8A-8D show modeled sinograms of a "stationary" scan data, which is the motion blurred attenuated projection of the axially short cylinder phantom.
Figure 8B:
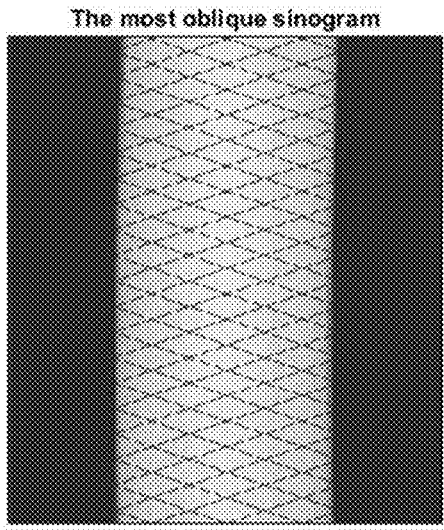
Figure 8C:
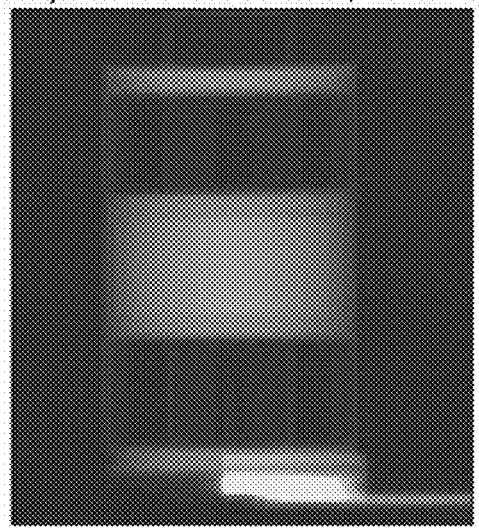
Figure 8D:
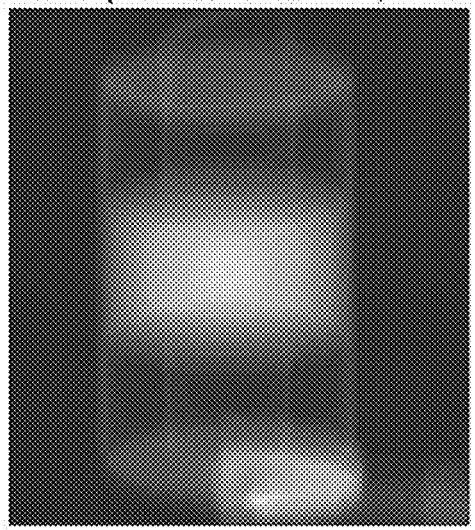

FIGS. 8A-8D show a modeled sinogram of a "stationary" scan data, which is the motion blurred attenuated projection of the axially short cylinder phantom. FIGS. 8A and 8B show activity sinograms of different polar angle segments. FIG. 8A is a direct plane sinogram. FIG. 8B is the most oblique sinogram. FIGS. 8C and 8D show attenuation factors, used in modeling of projection data. FIG. 8C is a direct plane attenuation factors, coronal view. FIG. 8D is the most oblique attenuation factors, coronal view. It can be mentioned that direct and oblique sinograms have different structures due to significant differences in attenuation. With oblique data, activity LOR may pass through the base of the cylindrical phantom in addition to its surface, which is the case with direct planes LORs. This example shows that the possible assumption of a uniform virtual cylinder, constructed by moving short cylinders, may be not adequate. Since the phantom was outside the FOV at the beginning and the end of acquisition, the projection data polar angle segments are uniform in the axial direction.

FIGS. 9A-9C show detector crystal TO estimations by two different methods and their differences. FIG. 9A shows the TO estimation by standard TA method. FIG. 9B shows the TO estimation by CBM TA method. FIG. 9C shows the difference. The difference is minimal and mostly attributed to estimation noise. The TO values are in TOF bin units (each 13 ps).

The line source TOF resolution was 205.32 ps after applying standard TA TOs. The CBM TOs led to a 205.61 ps TOF resolution of the same data set.

Figure 10A:
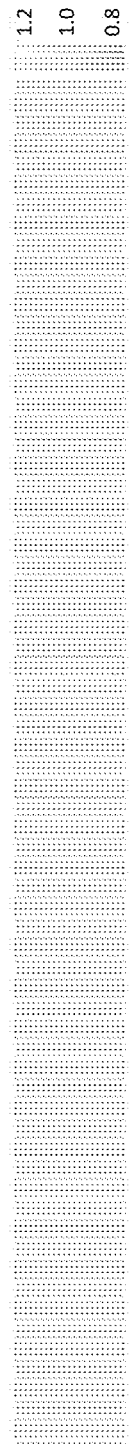
FIGS. 10A-10E show CE estimations for cases of standard and CBM setups.
Figure 10B:
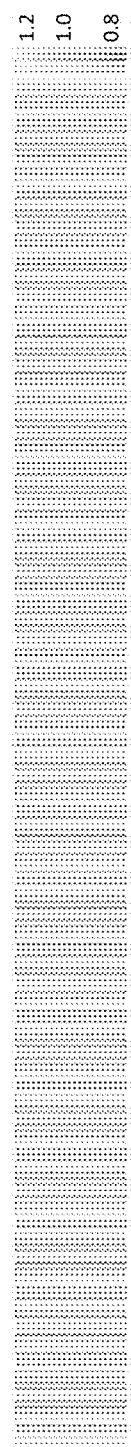
Figure 10C:
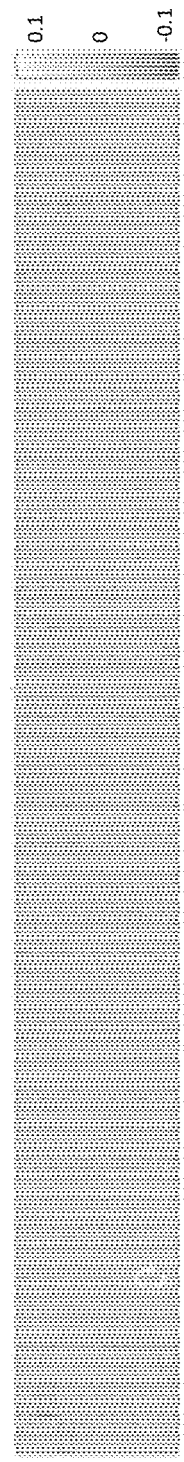
Figure 10D:
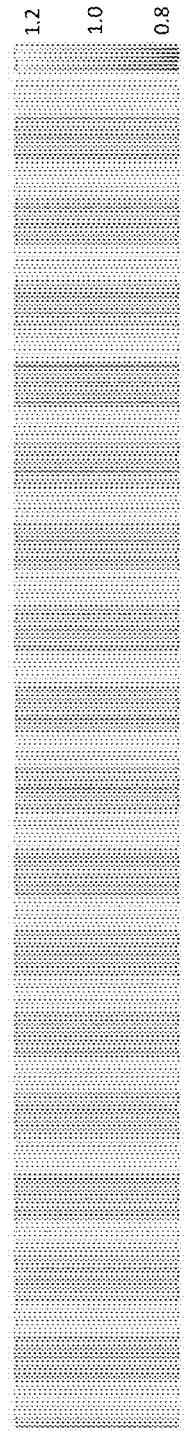
Figure 10E:
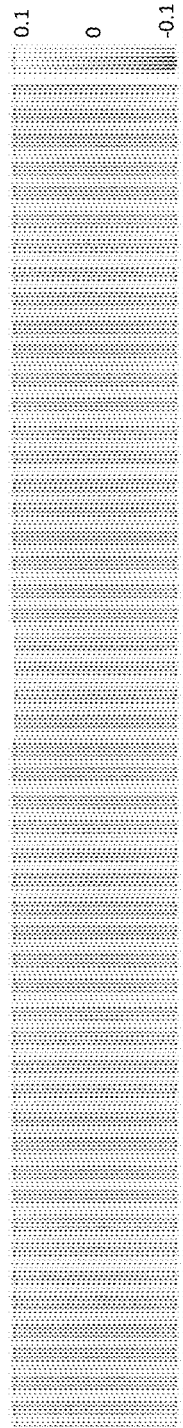

FIGS. 10A-10E show CE estimations for cases of standard and CBM setups. When the axially short cylinder phantom is properly modeled, a small difference is observed as a block edge pattern. With the virtual cylinder phantom, the difference is non-uniform across the axial direction. The unique LORs, where attenuation is only approximate, did not contribute to the edges of the axial FOV, where direct planes had proper attenuation. Such imbalance produced non-uniformity in the estimation of CE. FIG. 10A shows the CE estimation by a standard method. FIG. 10B shows the CE estimation using CBM axially short phantom TO. FIG. 10C shows the difference between the CE estimations shown in FIG. 10A and FIG. 10B. FIG. 10D shows CE estimation using virtual cylinder TO. FIG. 10E shows the difference between the CE estimations shown in FIG. 10A and FIG. 10D.

Figure 10F:
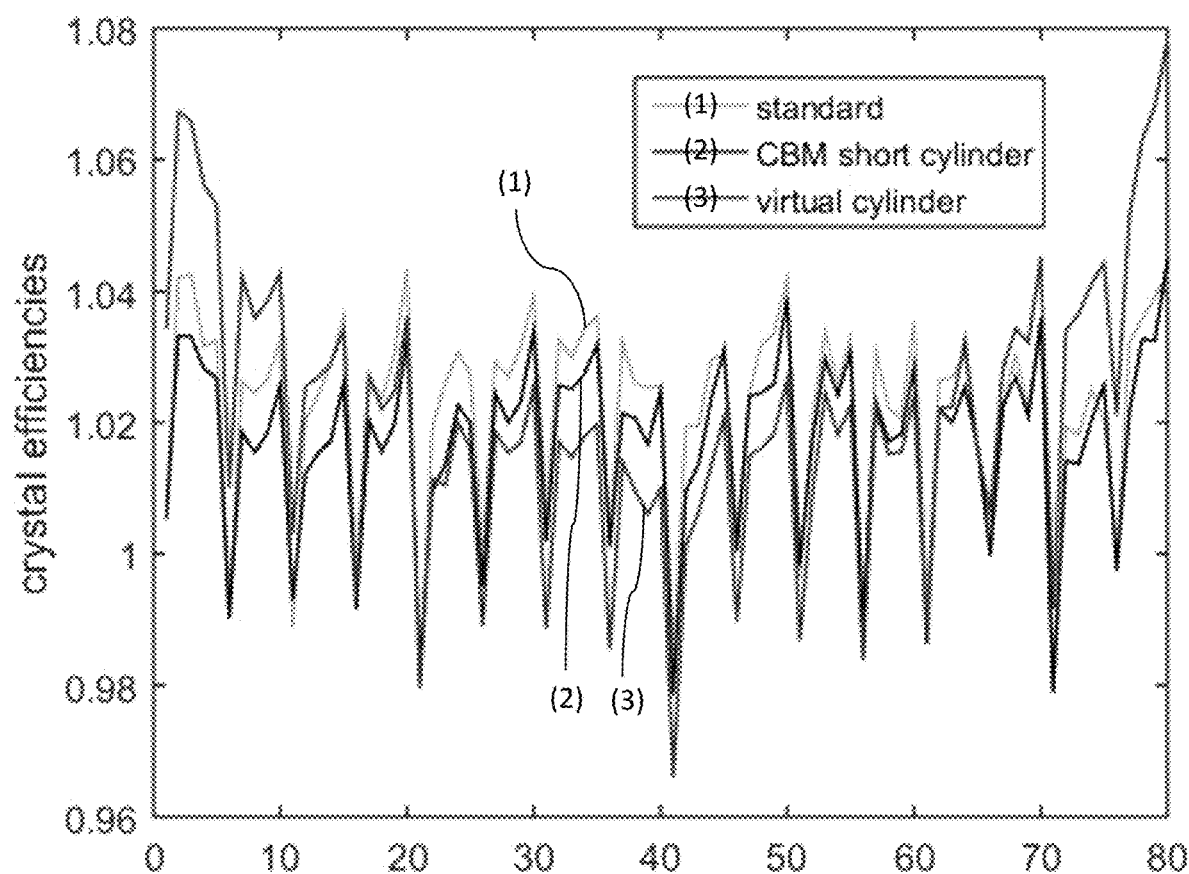

FIG. 10F shows axial profile of CE averaged over one detector module. The line (1) represents the CE estimation shown in FIG. 10A, the line (2) represents the CE estimation shown in FIG. 10B, and the line (3) represents the CE estimation shown in FIG. 10D.

FIGS. 11A and 11B examine CE estimation imperfection propagation into the cylinder image reconstruction. FIG. 11A shows the normalized difference image between reconstructions of uniform cylinder using CBM axially short cylinder phantom derived and standard normalization. FIG. 11B shows the normalized difference image between reconstructions of uniform cylinder using virtual cylinder derived and standard normalization. In both FIGS. 11A and 11B, the view on the top portion is the transaxial view and the view on the bottom portion is the coronal view.

The standard QC acquisition with standard QC normalization image reconstruction was used as a gold standard. Then, the CE component was replaced in the normalization array and data were reconstructed again. With the CBM axially short cylinder phantom derived CE component, the image difference showed small circular artifacts. These were attributed to the observed block edge pattern. With the virtual cylinder phantom derived CE component normalization, the image difference showed axial nonuniformity of about 5%, which can be attributed to axial nonuniformity of this CE component.

As PET scanner length becomes longer in an attempt to gain sensitivity, phantoms whose axial lengths are shorter than the scanner axial FOV is more desirable option than making longer phantoms for the system setup. The stationary scan can be used to cover only a portion of the available LORs. Since it is beneficial to cover all possible LORs, multiple or CBM scans can be exploited. The presented results verified that the CBM TA procedure using a short uniform cylindrical phantom produced the practically identical TO correction compared to standard TA.

Through employing CBM reconstruction, there is no need to make assumptions about virtual (no bed motion account) projection data. It allows the use of a more complicated phantom with additional fine structures, which can also cover other purposes such as spatial alignment of PET and CT scanners.

Additional Uses with Axially Short Phantom

The axially short phantom in CBM mode of the PET scanner can be used to check normalization coefficients for the PET detectors. By performing a PET scan while the axially short phantom is moved through the patient tunnel of the PET gantry, the uniformity of the PET detectors along the PET scanner FOV can be measured and used to determine the normalization coefficients for the detectors.

Additionally, since phantoms have uniform and known photon output, the axially short phantom 600 in a CBM setup can be used to check the alignment of the axial movement of the CBM bed 260 with the PET detectors by scanning the axially short phantom 600 in CBM mode. The method for checking the alignment of the axial movement of the CBM bed comprises acquiring list mode data from a PET scan of an axially short phantom in CBM mode; calculating the TOF center of mass of the axially short phantom from the list mode data; and comparing the calculated TOF center of mass of the axially short phantom to the center axis of the PET scanner's gantry.

Also, because the axially short phantom is light, it can be mounted to the CBM bed 260 in a cantilevered arrangement as shown in FIG. 7A. In this cantilevered arrangement, the axially short phantom 600 is situated extending away from and ahead of the CBM bed 260. By measuring and tracking the TOF COM of the axially short phantom as it moves through the PET gantry, the axial alignment of the CBM bed 260 can be checked.

The cantilevered arrangement for the axially short phantom 600 allows minimizing any attenuation effect of the CBM bed and the phantom holding hardware 280.

Although the subject matter has been described in terms of exemplary embodiments, it is not limited thereto. Rather, the appended claims should be construed broadly, to include other variants and embodiments, which may be made by those skilled in the art.

What is claimed is:

1. A method for time alignment in continuous bed motion (CBM) positron emission tomography (PET) scanner using an axially short phantom to cover long axial PET scanner's field of view, the method comprising:
    (a) receiving list mode data from PET scan of the axially short phantom in CBM mode;
    (b) generating CBM non-time of flight (TOF) projection data, scanner efficiency normalization array n, and attenuation factor a;
    (c) reconstructing image f from the CBM non-TOF projection data, corrected for scanner efficiency by the normalization array n, and for attenuation by the attenuation factor a;
    (d) modeling motion blurred non-TOF and TOF scatter S and motion blurred non-TOF and TOF projections $\bar{p}$;
    (e) for each line of response, estimating TOF center-of-mass (COM) of true coincidence distribution acquired in a stationary system of coordinates from zero order and first order moments $\bar{M}_0$ and $\bar{M}_1$ of the modeled TOF data;
    (f) for each line of response, computing measured TOF COM; and
    (g) determining TOF time offsets, to, by taking the difference between the measured TOF COM and the modeled TOF COM.

2. The method of claim 1, wherein the step (e) is carried out using the following expressions:

$$COM_{\rho\theta\zeta}^{model} = \frac{\bar{M}_1(\rho\theta\zeta)}{\bar{M}_0(\rho\theta\zeta)};$$

wherein $$\bar{M}_1(\rho\theta\zeta) = \sum_T T\bar{p}_{\rho\theta\zeta T}, \bar{M}_0(\rho\theta\zeta) = \sum_T \bar{p}_{\rho\theta\zeta T}; \text{ and}$$

$$\text{and } \bar{p}_{\rho\theta z T} = B\left(a_{\rho\theta\zeta}\sum_k C_{\rho\theta\zeta T,k}f_k + S_{\rho\theta\zeta T}\right);$$

wherein $(\rho,\theta,\zeta)$ is spatial projection index representing radial $(\rho)$, azimuthal $(\theta)$, and axial $(\zeta)$ projections, which includes polar angle segments;
wherein T is TOF bin index;
wherein $COM_{\rho\theta\zeta}^{model}$ is the estimated TOF COM data, $\bar{p}_{\rho\theta\zeta T}$ is the modeled TOF data, $\bar{M}_1(\rho\theta\zeta)$ is the first order moment of $\bar{p}_{\rho\theta\zeta T}$, $\bar{M}_0(\rho\theta\zeta)$ is the zero order moment of $\bar{p}_{\rho\theta\zeta T}$, and C is the geometrical projection system matrix; and and B is a blurring operator defined as $$B(\bar{p}_{\rho\theta\zeta T}) = \int_0^{t'_{acq}} dt' \sum_{\zeta} e^{-\lambda t} d_{\rho\theta z}(t) \bar{p}_{\rho\theta\zeta T} \delta_{z,Z(\zeta,t)}.$$

3. The method of claim 2, wherein the step (f) is carried out using the following expressions:

$$COM_{\rho\theta\zeta}^{measured} = \frac{n_{\rho\theta\zeta}M_1(\rho\theta\zeta)}{\bar{M}_0(\rho\theta\zeta)},$$

wherein $COM_{\rho\theta\zeta}^{measured}$ is the measured TOF COM and $$M_1(\rho\theta\zeta) = \sum_T T(y_{\rho\theta\zeta T} - r_{\rho\theta\zeta T}).$$

4. A non-transitory, machine-readable storage medium encoded with program instructions for controlling a continuous bed motion (CBM) PET scanner, such that when a processor executes the program instructions, the processor performs a method for time alignment of the CBM PET scanner, the method comprising:
    (a) receiving list mode data from PET scan of an axially short phantom in CBM mode;
    (b) generating CBM non-time of flight (TOF) projection data, scanner efficiency normalization array n, and attenuation factor a;
    (c) reconstructing image f from the CBM non-TOF projection data, corrected for scanner efficiency by the normalization array n, and for attenuation by the attenuation factor a;
    (d) modeling motion blurred non-TOF and TOF scatter S and motion blurred non-TOF and TOF projections $\bar{p}$;
    (e) for each line of response, estimating TOF center-of-mass (COM) of true coincidence distribution acquired in a stationary system of coordinates from zero order and first order moments $\bar{M}_0$ and $\bar{M}_1$ of the modeled TOF data;
    (f) for each line of response, computing measured TOF COM; and
    (g) determining TOF time offsets, to, by taking the difference between the measured TOF COM and the modeled TOF COM.

5. The non-transitory, machine-readable storage medium of claim 4, wherein the step (e) is carried out using the following expressions:

$$COM_{\rho\theta\zeta}^{model} = \frac{\bar{M}_1(\rho\theta\zeta)}{\bar{M}_0(\rho\theta\zeta)};$$

wherein $$\bar{M}_1(\rho\theta\zeta) = \sum_T T\bar{p}_{\rho\theta\zeta T}, \bar{M}_0(\rho\theta\zeta) = \sum_T \bar{p}_{\rho\theta\zeta T}; \text{ and}$$

$$\text{and } \bar{p}_{\rho\theta z T} = B\left(a_{\rho\theta\zeta}\sum_k C_{\rho\theta\zeta T,k}f_k + S_{\rho\theta\zeta T}\right);$$

wherein (ρ,θ,ζ) is spatial projection index representing radial (ρ), azimuthal (θ), and axial (ζ) projections, which includes polar angle segments;

wherein T is TOF bin index;

wherein $COM_{\rho\theta\zeta}^{Model}$ is the estimated TOF COM data, $\bar{p}_{\rho\theta\zeta T}$ is the modeled TOF data, $\bar{M}_1(\rho\theta\zeta)$ is the first order moment of $\bar{p}_{\rho\theta\zeta T}$, $\bar{M}_0(\rho\theta\zeta)$ is the zero order moment of $\bar{p}_{\rho\theta\zeta T}$, and C is the geometrical projection system matrix; and and B is a blurring operator defined as $$B(\bar{p}_{\rho\theta\zeta T}) = \int_0^{t'_{acq}} dt' \sum_\zeta e^{-\lambda t} d_{\rho\theta z}(t) \bar{p}_{\rho\theta\zeta T} \delta_{z,Z(\zeta,t)}.$$

6. The non-transitory, machine-readable storage medium of claim 5, wherein the step (f) is carried out using the following expressions:

$$COM_{\rho\theta\zeta}^{measured} = \frac{n_{\rho\theta\zeta} M_1(\rho\theta\zeta)}{\overline{M}_0(\rho\theta\zeta)},$$

wherein $COM_{\rho\theta\zeta}^{measured}$ is the measured TOF COM and $$M_1(\rho\theta\zeta) = \sum_T T(y_{\rho\theta\zeta T} - r_{\rho\theta\zeta T}).$$

7. A method for checking normalization coefficients for positron emission tomography (PET) detectors in a continuous bed motion (CBM) PET scanner comprising:

performing a PET scan while an axially short phantom is moving through a patient tunnel of the PET scanner, measuring the uniformity of the PET detectors along the PET scanner's field of view; and determining normalization coefficients for the detectors.

\* \* \* \* \*